(12) United States Patent
Ali et al.

(10) Patent No.: US 9,745,282 B2
(45) Date of Patent: Aug. 29, 2017

(54) INDOLINE COMPOUNDS AS ALDOSTERONE SYNTHASE INHIBITORS

(71) Applicants: Merck Sharp & Dohme Corp., Rahway, NJ (US); ElexoPharm GmbH, Saarbrucken (DE)

(72) Inventors: Amjad Ali, Freehold, NJ (US); Michael Man-Chu Lo, Edison, NJ (US); Edward Metzger, Somerset, NJ (US); Lina Yin, Saarbrucken (DE); Rolf Hartmann, Saarbrucken (DE); Qingzhong Hu, Saarbrucken (DE); Ralf Heim, Saarbrucken (DE); Christina Zimmer, Volklingen (DE)

(73) Assignees: Merck Sharp & Dohme Corp, Rahway, NJ (US); ElexoPharm GmbH, Saarbrucken (DE)

( * ) Notice: Subject to any disclaimer, the term of this patent is extended or adjusted under 35 U.S.C. 154(b) by 0 days.

(21) Appl. No.: 15/197,957

(22) Filed: Jun. 30, 2016

(65) Prior Publication Data

US 2016/0304486 A1    Oct. 20, 2016

Related U.S. Application Data

(63) Continuation of application No. 14/433,441, filed as application No. PCT/US2013/062975 on Oct. 2, 2013, now Pat. No. 9,550,750.

(60) Provisional application No. 61/710,197, filed on Oct. 5, 2012.

(51) Int. Cl.
| | |
|---|---|
| *C07D 401/04* | (2006.01) |
| *A61K 31/4709* | (2006.01) |
| *A61K 31/4439* | (2006.01) |
| *A61K 45/06* | (2006.01) |
| *C07D 409/14* | (2006.01) |
| *A61K 31/4725* | (2006.01) |

(52) U.S. Cl.
CPC ........ *C07D 401/04* (2013.01); *A61K 31/4439* (2013.01); *A61K 31/4709* (2013.01); *A61K 31/4725* (2013.01); *A61K 45/06* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 8,030,334 B2 | 10/2011 | Adams et al. | |
| 8,410,273 B2 * | 4/2013 | Kanno | C07D 217/14 546/122 |
| 2009/0105231 A1 | 4/2009 | Sawada et al. | |
| 2009/0221591 A1 | 9/2009 | Hartmann et al. | |
| 2010/0216694 A1 | 8/2010 | Liang et al. | |
| 2010/0292225 A1 | 11/2010 | Chamoin et al. | |
| 2011/0112067 A1 | 5/2011 | Hartmann et al. | |
| 2012/0077828 A1 | 3/2012 | Axten et al. | |

FOREIGN PATENT DOCUMENTS

| | | |
|---|---|---|
| EP | 2418203 A1 | 2/2012 |
| EP | 3055288 A1 | 8/2016 |
| FR | 2530246 A1 | 7/1982 |
| WO | WO9321178 A1 | 10/1993 |
| WO | WO0132621 A1 | 5/2001 |
| WO | WO03027094 A1 | 4/2003 |
| WO | WO 2005/110410 A2 * | 11/2005 |
| WO | WO 2006/020049 A2 * | 2/2006 |
| WO | WO2007030559 A2 | 3/2007 |
| WO | WO2007098418 A1 | 8/2007 |
| WO | WO2009111056 A1 | 9/2009 |
| WO | WO 2010/116915 A1 * | 10/2010 |
| WO | WO2010130794 A1 | 11/2010 |
| WO | WO2011061168 | 5/2011 |
| WO | WO2011095196 A1 | 8/2011 |
| WO | WO2011149921 A1 | 12/2011 |
| WO | WO2012012478 A1 | 1/2012 |
| WO | WO2012112961 A1 | 8/2012 |
| WO | WO2015051725 A1 | 4/2015 |

OTHER PUBLICATIONS

International Search Report for PCT/US2013/062975, mailed on Feb. 11, 2014, 14 pages.
Main, C. A. et al., High throughput synthesis of diverse 2,5-disubstituted indoles using titanium carbenoids bearing boronate functionality, Tetrahedron, 2008, p. 901-914, vol. 64.
U.S. Appl. No. 14/433,441, filed Apr. 3, 2015.

* cited by examiner

*Primary Examiner* — Zinna Northington Davis
(74) *Attorney, Agent, or Firm* — Janet E. Fair; Catherine D. Fitch

(57) ABSTRACT

This invention relates to indoline compounds of the structural formula:

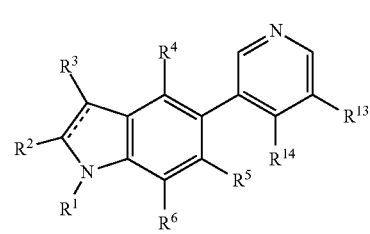

or their pharmaceutically acceptable salts, wherein the variables are defined herein. The inventive compounds selectively inhibit aldosterone synthase. This invention also provides for pharmaceutical compositions comprising the compounds of Formula I or their salts as well as potentially to methods for the treatment, amelioration or prevention of conditions that could be treated by inhibiting aldosterone synthase.

10 Claims, No Drawings

INDOLINE COMPOUNDS AS ALDOSTERONE SYNTHASE INHIBITORS

CROSS-REFERENCE TO RELATED APPLICATIONS

The present application is a continuation of application U.S. Ser. No. 14/433,441 which is a U.S. National Phase application under 35 U.S.C. §371 of PCT Application No. PCT/US2013/062975, filed Oct. 2, 2013, which published as WO2014/055595 A1 on Apr. 10, 2014 which claims priority to U.S. provisional application Ser. No. 61/710,197, filed Oct. 5, 2012, the contents of which are hereby incorporated by reference in their entirety.

FIELD OF THE INVENTION

The present invention relates indoline compounds, which selectively inhibit aldosterone synthase (CYP11B2) with diminished inhibition or affect on steroid-11-β-hydroxylase (CYP11B1) inhibitors. The inventive compounds potentially have utility in treating cardiovascular diseases such as hypertension or heart failure. The present invention also relates to pharmaceutical compositions comprising the inventive compounds as well as processes for their preparation.

BACKGROUND OF THE INVENTION

Aldosterone is a steroid hormone secreted in the adrenal cortex. In primary cells of the distal tubules and collecting ducts of the kidney, aldosterone binding to the mineralocorticoid receptor (MR) results in the retention of sodium and water and excretion of potassium, which in turn leads to increased blood pressure. Aldosterone also causes inflammation that leads to fibrosis and remodeling in the heart, vasculature and kidney. This inflammation may proceed by MR-dependent as well as MR-independent mechanisms (Gilbert, K. C. et al., Curr. Opin. Endocrinol. Diabetes Obes., vol. 17, 2010, pp. 199-204).

Mineralocorticoid receptor antagonists (MRAs), such as spironolactone and eplerenone, have been used previously to block the effects of aldosterone binding to MR. When given in addition to standard therapies such as angiotensin-converting enzyme (ACE) inhibitors and loop diuretics, the nonselective MRA spironolactone and the selective MRA eplerenone significantly reduced morbidity and mortality in patients with heart failure or myocardial infarction (Pitt, B. et al., New Engl. J. Med., vol. 341, 1999, pp. 709-717; Pitt, B. et al., New Engl. J. Med., vol. 348, 2003, pp. 1382-1390). However, the nonselective MRA spironolactone can also bind to and act at other steroid receptors, and as a consequence its use is associated with sexual side effects such as gynecomastia, dysmenorrhoea and impotence (Pitt, B. et al., New Engl. J. Med., vol. 341, 1999, pp. 709-717; MacFadyen, R. J. et al., Cardiovasc. Res., vol. 35, 1997, pp 30-34; Soberman, J. E. et al., Curr. Hypertens. Rep., vol. 2, 2000, pp 451-456). Additionally, both spironolactone and eplerenone are known to cause elevated plasma potassium levels (hyperkalemia) and elevated aldosterone levels.

An alternative method of blocking the effects of aldosterone is to inhibit its biosynthesis. CYP11B2 is a mitochondrial cytochrome P450 enzyme that catalyzes the final oxidative steps in the conversion of 11-deoxycorticosterone, a steroidal precursor, to aldosterone (Kawamoto, T. et al., Proc. Natl. Acad. Sci. USA, vol. 89, 1992, pp. 1458-1462). Compounds that inhibit CYP11B2 should thus inhibit the formation of aldosterone. Such compounds, particularly those of nonsteroidal structure, should provide the beneficial effects of MRAs, without the adverse effects derived from steroid receptor binding or MR-independent inflammatory pathways. The art has recognized that reducing aldosterone levels by inhibiting aldosterone synthase could represent a new pharmaceutical strategy that might be useful in treating a disorder or disease characterized by increased stress hormone levels and/or decreased androgen hormone levels in a patient (WO2011/088188 to Novartis). Compounds possessing this activity might be expected to treat disease states such as heart failure, cachexia, acute coronary syndrome, Cushing's syndrome or metabolic syndrome.

CYP11B1 is a related enzyme that catalyzes the formation of glucocorticoids, such as cortisol, an important regulator of glucose metabolism. Because human CYP11B2 and CYP11B1 are greater than 93% homologous, it is possible for nonselective compounds to inhibit both enzymes (Kawamoto, T. et al., Proc. Natl. Acad. Sci. USA, vol. 89, 1992, pp 1458-1462; Taymans, S. E. et al., J. Clin. Endocrinol. Metab., vol. 83, 1998, pp 1033-1036). It would be preferable, however, for therapeutic agents to selectively inhibit CYP11B2 and the formation of aldosterone with diminished inhibition of, or affect on, CYP11B1 and the production of cortisol.

WO 2009/135651 to Elexopharm describes 6-pyridin-3yl-3,4,-dihydro-1H-quinolin-2-one derivatives as being CYP11B2 inhibitors. Two compounds described therein are lactam derivatives of the formula:

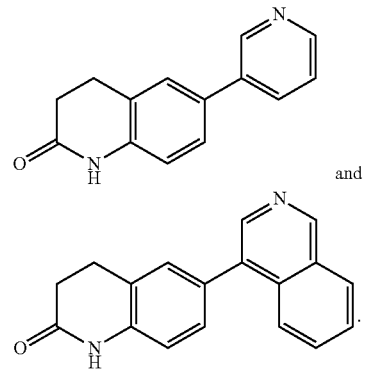

and

Structurally similar lactam and thiolactam compounds are disclosed by Lucas et al., J. Med. Chem. 2008, 51, 8077-8087; those compounds are said to be potential inhibitors of CYP11B2. Lucas et al. in J. Med. Chem. 2011, 54, 2307-2309 describes certain pyridine substituted 3,4-dihydro-1H-quinolin-2-ones as being highly potent as selective inhibitors of CYP11B2. An abstract of a thesis reports that a series of novel heterocyclic-substituted 4,5-dihydro-[1,2,4]triazolo[4,3a]quinolones was evaluated for its aldosterone synthase activity; one of the compounds is reported as exhibiting excellent selectivity of CYP11B2 over CYP11B1.

Benzimidazole derivatives are known in the art to treat various disease states. For example, U.S. Pat. No. 6,897,208 to Aventis Pharmaceuticals describes compounds of the formula:

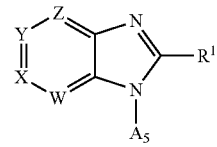

wherein $R^1$ is an optionally substituted aryl or heteroaryl group and $A_5$ is H or alkyl. These compounds are said to be kinase inhibitors. Other benzimidazoles derivatives are known in the art. For example, WO2002/46168 A1 to AstraZeneca describes benzimidazoles derivatives that are useful in the treatment or prophylaxis of Alzheimer's disease, anxiety disorders, depressive disorders, osteoporosis, cardiovascular disease, rheumatoid arthritis or prostate cancer. US2007/0270420 A1 to Vertex Pharmaceuticals describes benzimidazole compounds that are useful of inhibitors of GSK-3 and Lck protein kineases. WO2012/012478 to Merck describes benzimidazole compounds that are effective at selectivity inhibiting CYP11B2. Other benzimidazole derivatives are described in US 2009/0018124 A1, WO2004/082638 A1, WO2008/073451 A1 and US 2005/0272756 A1.

Novartis in US 2010/0261698 A1 describes indole derivatives of the formula:

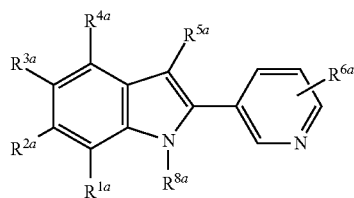

Novartis indicates that these compounds inhibit aldosterone synthase and may be useful in the treatment of disease states such as heart failure and hypertension. In WO2010/130,796 A1 and WO2011/061168, Novartis discloses aryl-pyridine derivatives that are said to inhibit aldosterone synthase.

US 2009/0221591 A1 to Universitat des Saarlandes also discloses compounds that inhibit CYP11B1 and CYP11B2. WO 2009/135651 to Universitat des Saarlandes teaches that compounds of the formula:

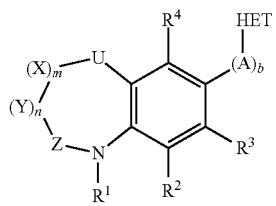

possess the ability to inhibit aldosterone synthase.

WO1999/400094 Bayer AG discloses oxazolidinones with azol-containing tricycles as having antibacterial activity.

U.S. Pat. No. 7,381,825 to Takeda describes histone deacetylase inhibitors of the formula

Z-Q-L-M where Q is a substituted or unsubstituted aromatic ring, L is a substituent providing between 0-10 atoms separation between M and the remainder of the compound, M is a substituent capable of complexing with a deacetylase catalytic site and/or metal ion, and Z is list of bicyclic groups, including, but not limited to:

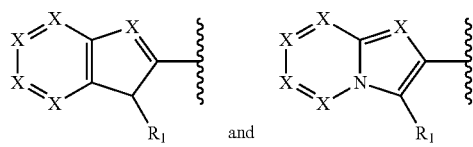

where X is $CR_{12}$ or N. These compounds are said to be useful in treating cell-proliferative diseases such as, for example, leukemia, melanoma, bladder cancer, etc.

FR 2 530 246 to Delalande SA describes pyridyl-substituted indoline compounds of the formula:

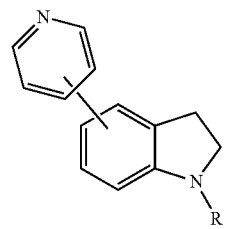

where R may be groups such as H, —COCH$_3$ and benzyl, as possessing cardiovascular utility.

Other heterocyclic substituted indoline derivatives are described in WO 2011/119663 to GlaxoSmithKline, WO1998/46605 and WO 2000/23444 to Abbott Laboratories, WO 2011/095196 to Merck GmbH, U.S. Pat. No. 7,872,031 to Vertex Pharmaceuticals. None of the compounds disclosed these published applications is taught to be inhibitors of aldosterone synthase.

SUMMARY OF THE INVENTION

In its many embodiments, the present invention provides for novel indoline compounds, which are inhibitors of CYP11B2, or metabolites, stereoisomers, salts, solvates or polymorphs thereof, processes of preparing such compounds, pharmaceutical compositions comprising one or more such compounds, processes of preparing pharmaceutical compositions comprising one or more such compounds and potentially methods of treatment, inhibition or amelioration of one or more disease states associated with inhibiting CYP11B2 by administering an effective amount at least one of the inventive indoline compounds to a patient in need thereof.

In one aspect, the present application discloses a compound or a pharmaceutically acceptable salt, metabolite, solvate, prodrug or polymorph of said compound, said compound having the general structure shown in Formula I

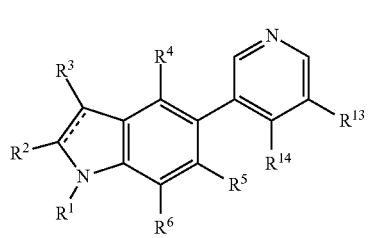

wherein:
$R^1$ is —C(O)R$^7$; —C(O)OR$^7$; —C(O)N(R$^{11}$)(R$^{12}$); —C(S)R$^7$; —S(O)$_2$R$^7$; alkyl which is optionally substituted on or more times (e.g., 1 to 4 times) by halogen; cycloalkyl, which is optionally substituted one or more times (e.g., 1 to 4) by halogen, alkyl or haloalkyl; aryl optionally substituted one or more times (e.g., 1 to 4 times) by halogen, alkyl, haloalkyl, cycloalkyl, —OR$^7$, —CN, —NR$^8$R$^9$ —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; arylalkyl, wherein the aryl ring is optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; heteroaryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; or arylalkylcarbonyl, wherein the aryl ring is optionally substituted one or more times by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$;

R$^2$ is H; halogen; —CN; —OR$^7$; —N(R$^{10}$)C(O)R$^7$; —NR$^{11}$R$^{12}$; —C(O)R$^7$; —C(O)N(R$^{11}$)(R$^{12}$); —N(R$^{10}$)C(O)—R$^7$; —C(O)OR$^7$; —OC(O)R$^7$; —SO$_2$N(R$^{11}$)(R$^{12}$); —N(R$^{10}$)SO$_2$—R$^7$; —S(O)$_m$—R$^7$; alkyl optionally substituted one or more times (e.g., 1 to 4 times) by halogen, —OR$^7$, NR$^8$R$^9$, —CN, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; or heteroaryl optionally substituted one or more times (e.g., 1 to 4 times) by halogen, alkyl, haloalkyl, cycloalkyl, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$;

R$^3$ is H; halogen; —CN; —OR$^7$; —N(R$^{10}$)C(O)R$^7$; —NR$^{11}$R$^{12}$; —C(O)R$^7$; —C(O)N(R$^{11}$)(R$^{12}$); —N(R$^{10}$)C(O)—R$^7$; —C(O)OR$^7$; —OC(O)R$^7$; —SO$_2$N(R$^{11}$)(R$^{12}$); —N(R$^{10}$)SO$_2$—R$^7$; —S(O)$_m$—R$^7$; alkyl optionally substituted one or more times (e.g., 1 to 4 times) by halogen, —OR$^7$, NR$^8$R$^9$, —CN, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$;

R$^4$ is H; halogen; —CN; alkyl optionally substituted one or more times (e.g., 1 to 4 times) by halogen or cycloalkyl optionally substituted once or twice by alkyl or halogen; or cycloalkyl optionally substituted once or twice by alkyl or halogen;

R$^5$ is H; halogen; —CN; alkyl optionally substituted one or more times (e.g., 1 to 4 times) by halogen or cycloalkyl optionally substituted once or twice by alkyl or halogen; or cycloalkyl optionally substituted once or twice by alkyl or halogen;

R$^6$ is H; halogen; —CN; alkyl optionally substituted one or more times (e.g., 1 to 4 times) by halogen or cycloalkyl optionally substituted once or twice by alkyl or halogen; or cycloalkyl optionally substituted once or twice by alkyl or halogen;

R$^7$ is independently H; alkyl optionally substituted one or more times (e.g., 1 to 4 times) by halogen, —OR$^{10}$, —NR$^8$R$^9$, —CN, —N(R$^{10}$)C(O)R$^{10}$, —C(O)N(R$^8$)(R$^9$), —C(O)R$^{10}$, —C(O)OR$^{10}$ or —S(O)$_m$—R$^{10}$; cycloalkyl optionally substituted one or more times (e.g., 1 to 4 times) by halogen, alkyl, haloalkyl, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; aryl optionally substituted one or more times (e.g., 1 to 4 times) by halogen, alkyl, haloalkyl, cycloalkyl, —OR$^{10}$, —NR$^8$R$^9$, —CN, —N(R$^{10}$)C(O)R$^{10}$, —C(O)N(R$^8$)(R$^9$), —C(O)R$^{10}$, —C(O)OR$^{10}$—OC(O)R$^{10}$, or —S(O)$_m$—R$^{10}$; or heteroaryl optionally substituted one or more times (e.g., 1 to 4 times) by halogen, alkyl, haloalkyl, cycloalkyl, —OR$^{10}$, —NR$^8$R$^9$, —CN, —N(R$^9$)C(O)R$^{10}$, —C(O)N(R$^8$)(R$^9$), —C(O)R$^{10}$, —C(O)OR$^{10}$—OC(O)R$^{10}$ or —S(O)$_m$—R$^{10}$;

R$^8$ is independently H or alkyl;

R$^9$ is independently H or alkyl;

or R$^8$ and R$^9$ are joined together with the nitrogen to which they are attached form a saturated 5- to 7-membered heterocyclic ring;

R$^{10}$ is independently H, alkyl or haloalkyl;

R$^{11}$ is independently H; alkyl optionally substituted one or more times (e.g., 1 to 4 times) by halogen, —OR$^7$, —NR$^8$R$^9$, —CN, —N(R$^{10}$)C(O)R$^7$, —C(O)N(R$^8$)(R$^9$), —C(O)R$^7$, —C(O)OR$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^8$ or —S(O)$_m$—R$^8$; aryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)(R$^7$), —C(O)N(R$^7$)(R$^8$), —C(O)R$^7$, —C(O)OR$^7$, —OC(O)R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$;

R$^{12}$ is independently H; alkyl optionally substituted one or more times (e.g., 1 to 4 times) by halogen, —OR$^7$, —NR$^8$R$^9$, —CN, —N(R$^{10}$)C(O)R$^7$, —C(O)N(R$^8$)(R$^9$), —C(O)R$^7$, —C(O)OR$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^8$ or —S(O)$_m$—R$^8$; aryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)(R$^7$), —C(O)N(R$^7$)(R$^8$), —C(O)R$^7$, —C(O)OR$^7$, —OC(O)R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$;

or R$^{11}$ and R$^{12}$ are joined together with the nitrogen to which they are attached form a saturated 5- to 7-membered heterocyclic ring;

R$^{13}$ is H; halogen; —CN; —OR$^7$; —NR$^{11}$R$^{12}$; —N(R$^{10}$)C(O)R$^7$; —C(O)N(R$^{11}$)(R$^{12}$); —C(O)R$^7$; —C(O)OR$^7$; —OC(O)R$^7$; —SO$_2$N(R$^{11}$)(R$^{12}$); —N(R$^{10}$)SO$_2$—R$^7$; —S(O)$_m$—R$^7$; alkyl optionally substituted one or more times (e.g., 1 to 4 times) by halogen, —OR$^7$, —NR$^8$R$^9$, —CN, —N(R$^{11}$)C(O)R$^7$, —C(O)N(R$^8$)(R$^9$), —C(O)OR$^7$, —OC(O)R$^7$, —SO$_2$N(R$^8$)(R$^9$), —N(R$^{10}$)SO$_2$—R$^7$, or —S(O)$_m$—R$^7$; cycloalkyl optionally substituted one or more times (e.g., 1 to 4 times) by halogen, alkyl, haloalkyl, —NR$^8$R$^9$, —CN, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)(R$^7$), —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; or monocyclic heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$;

R$^{14}$ is H; halogen; —CN; —OR$^7$; —NR$^{11}$R$^{12}$; —N(R$^{10}$)C(O)R$^7$; —(C(O)N(R$^{11}$)(R$^{12}$); —C(O)R$^7$; —C(O)OR$^7$; —OC(O)R$^7$; —SO$_2$N(R$^{11}$)(R$^{12}$); —N(R$^{10}$)SO$_2$—R$^7$; —S(O)$_m$—R$^7$; alkyl optionally substituted one or more times (e.g., 1 to 4 times) by halogen, —OR$^7$, —NR$^8$R$^9$, —CN, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$; or monocyclic heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^8$)(R$^9$), —N(R$^{10}$)SO$_2$—R$^7$ or —S(O)$_m$—R$^7$;

or R$^{13}$ and R$^{14}$ are joined together to form a 5-7 membered carbocyclic or heterocyclic ring that is fused to the pyridyl ring to which R$^{13}$ and R$^{14}$ are attached, wherein the ring formed by R$^{13}$ and R$^{14}$ is optionally substituted by 1 to 3 R$^{15}$;

R$^{15}$ is independently H; halogen; —CN; —OR$^7$; —C(O)N(R$^8$)(R$^9$); —C(O)R$^7$; —C(O)OR$^7$; —OC(O)R$^7$; —SO$_2$N(R$^8$)(R$^9$); —N(R$^{10}$)SO$_2$—R$^7$; —S(O)$_m$—R$^7$; alkyl optionally substituted one or more times (e.g., 1 to 4 times) by halogen, —OR$^7$, —NR$^8$R$^9$, —CN, —N(R$^{11}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)S(O)$_2$—R$^7$, or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^8$, —SO$_2$N(R$^8$)(R$^9$), —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)(R$^7$), —C(O)N(R$^8$)(R$^9$), —C(O)R$^7$—C(O)OR$^7$, —OC(O)R$^7$, —SO$_2$N(R$^8$)(R$^9$), —N(R$^{10}$)SO$_2$—R$^7$, or —S(O)$_m$—R$^7$; heterocycloalkyl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$;

==== is a single or double bond; and m is 0, 1 or 2;

provided that when R$^1$ is —C(O)alkyl, R$^5$, R$^6$ R$^{13}$ and R$^{14}$ cannot all be hydrogen at the same time and further provided that monocyclic heteroaryl cannot be a tetrazole ring.

Another aspect of the present invention is pharmaceutical compositions comprising a therapeutically effective amount of at least one compound of Formula I or a pharmaceutically acceptable salt thereof and a pharmaceutically acceptable carrier.

Another aspect of the present invention is pharmaceutical compositions comprising a therapeutically effective amount of at least one compound of Formula I or a pharmaceutically acceptable salt thereof, a therapeutically effective amount of at least one additional therapeutic agent and a pharmaceutically acceptable carrier.

Another aspect of the present invention potentially is the prevention of one or more disease states associated with inhibiting CPY11B2 by administering an effective amount of at least one of the inventive imidazopyridyl compounds to a patient in need thereof.

It is further contemplated that the combination of the invention could be provided as a kit comprising in a single package at least one compound of Formula I or a pharmaceutically acceptable salt thereof in a pharmaceutical composition, and at least one separate pharmaceutical composition, such as, for example a separate pharmaceutical composition comprising a therapeutic agent.

The compounds of the present invention could be useful in the treatment, amelioration or prevention of one or more conditions associated with inhibiting CYP11B2 by administering a therapeutically effective amount of at least one compound of Formula I or a pharmaceutically acceptable salt thereof to a mammal in need of such treatment. Conditions that could be treated or prevented by inhibiting CYP11B2 include hypertension, heart failure such as congestive heart failure, diastolic dysfunction, left ventricular diastolic dysfunction, heart failure (including congestive heart failure), diastolic dysfunction, left ventricular diastolic dysfunction, diastolic heart failure, systolic dysfunction, hypokalemia, renal failure (including chronic renal failure), restenosis, syndrome X, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, ischemia, myocardial and vascular fibrosis, myocardial necrotic lesions, vascular damage, myocardial necrotic lesions, vascular damage, myocardial infarction, left ventricular hypertrophy, cardiac lesions, vascular wall hypertrophy, endothelial thickening or fibrinoid necrosis of coronary arteries.

The compounds of the present invention also might be useful in treating one or more conditions characterized by increased stress hormone levels and/or decreased androgen hormone levels in a mammal by administering a therapeutically effective amount of at least one compound of Formula I or a pharmaceutically acceptable salt thereof to a mammal in need of such treatment. Conditions characterized by increased stress hormone levels and/or decreased androgen hormone levels in a mammal include, for example, heart failure (e.g., acute heart failure, acute decompensated heart failure, chronic heart failure, chronic heart failure with impaired exercise tolerance or chromic heart failure with muscle weakness), cachexia (e.g., cardiac cachexia, COPD-induced cachexia, cirrhosis-induced cachexia, tumor-induced cachexia or viral (HIV)-induced cachexia), acute coronary syndrome, Cushing's syndrome or metabolic syndrome.

Another aspect of the present invention could be the use of a compound of Formula I or a pharmaceutically acceptable salt thereof for the manufacture of a medicament for the treatment, amelioration or prevention of one or more conditions associated with inhibiting CYP11B2 in a patient.

Another aspect of the present invention could be the use of a compound of Formula I or a pharmaceutically acceptable salt thereof for the manufacture of a medicament for the treatment, amelioration or prevention of one or more conditions associated with inhibiting CYP11B2 in a patient.

This invention further relates to process for the preparation of the compounds of Formula I or their pharmaceutically acceptable salts. Moreover, this invention also relates to the use of the compounds of Formula I or their pharmaceutically acceptable salts to validate in vitro assays, such as, for example the V79-Human-CYP11B2 and V79-Human-CYP11B1 discussed later in the application.

These and other objectives will be evident from the description of the invention contained herein.

DETAILED DESCRIPTION

In an embodiment, the present invention provides compounds represented by structural Formula I or pharmaceutically acceptable salt thereof, wherein the various moieties are as described as above.

Another embodiment of the present invention is compounds of Formula I or their pharmaceutically acceptable salts wherein ==== is a single bond.

Another embodiment of the present invention is compounds of Formula I or their pharmaceutically acceptable salts wherein ==== is a double bond.

Another embodiment of the present invention is compounds or their pharmaceutically acceptable salts of Formula I represented by structural Formula II

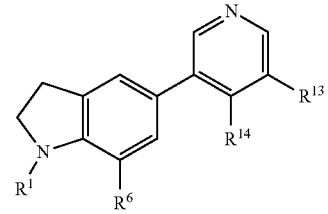

wherein $R^1$, $R^6$, $R^{13}$ and $R^{14}$ are as defined in Formula I.

Another embodiment of the present invention is compounds or their pharmaceutically acceptable salts of Formula I represented by structural Formula III

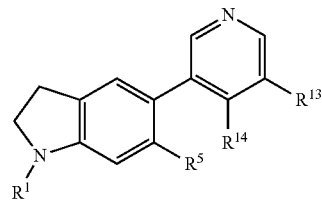

wherein $R^1$, $R^5$, $R^{13}$ and $R^{14}$ are as defined in Formula I.

Another embodiment of the present invention is compounds or their pharmaceutically acceptable salts of Formula I represented by structural Formula IV

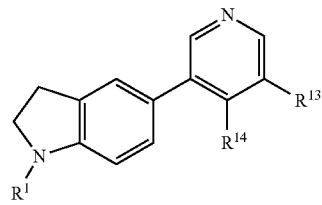

wherein $R^1$, $R^{13}$ and $R^{14}$ are as defined in Formula I.

Another embodiment of the present invention is compounds or their pharmaceutically acceptable salts of Formula I represented by structural Formula V

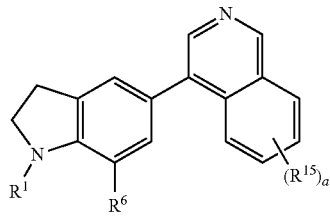

wherein $R^1$, $R^6$ and $R^{15}$ are as defined in Formula I and a is 0, 1 or 2.

Another embodiment of the present invention is compounds or their pharmaceutically acceptable salts of Formula V, wherein $R^1$, $R^2$, $R^3$ and are as defined in Formula I and a is 0 (i.e., $R^{15}$ is absent), or wherein a is 1 or 2 and $R^{15}$ is alkyl or halo.

Another embodiment of the present invention is compounds or their pharmaceutically acceptable salts of any of the embodiments of Formulae I through V, wherein $R^1$ is —C(O)$R^7$, —C(O)O$R^7$, or —C(O)N($R^{11}$)($R^{12}$), wherein $R^7$, $R^{11}$ or $R^{12}$ is as defined as in Formula I.

Another embodiment of the present invention is compounds or their pharmaceutically acceptable salts of any of the embodiments of Formulae I through V, wherein $R^1$ is arylalkylcarbonyl, wherein the aryl ring (e.g., phenyl) is optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$, wherein $R^7$, $R^8$, $R^9$, $R^{10}$ and m are as defined in Formula I (e.g., alkyl).

Another embodiment of the present invention is compounds or their pharmaceutically acceptable salts of any of the embodiments of Formulae I through V, wherein $R^1$ is —C(O)$R^7$, —C(O)O$R^7$, or —C(O)N($R^{11}$)($R^{12}$), wherein $R^7$ is alkyl (e.g., methyl, ethyl, n-propyl, i-propyl, n-butyl, iso-butyl, sec-butyl, tert-butyl) or aryl (e,g, phenyl) or aryl (e.g. phenyl) substituted one or twice by halogen, —O$R^7$ (where $R^7$ is H, alkyl (e.g., methyl, ethyl, n-propyl, i-propyl, n-butyl, iso-butyl, sec-butyl, tert-butyl) or haloalkyl (e.g., —CF$_3$)) or haloalkyl (e.g., —CF$_3$); $R^{11}$ is H; and $R^{12}$ is alkyl (e.g., methyl, ethyl, n-propyl, i-propyl, n-butyl, iso-butyl, sec-butyl, tert-butyl) or aryl (e,g, phenyl) or aryl (e.g. phenyl) substituted one or twice by halogen, —O$R^7$ (where $R^7$ is H, alkyl (e.g., methyl, ethyl, n-propyl, i-propyl, n-butyl, iso-butyl, sec-butyl, tert-butyl) or haloalkyl (e.g., —CF$_3$)) or haloalkyl (e.g., —CF$_3$).

Another embodiment of the present invention is compound or their pharmaceutically acceptable salts of any of the embodiments of Formulae I through V wherein $R^1$ is —C(O)$R^7$ and $R^7$ is or heteroaryl (e.g., a thienyl, furanyl or pyrazolyl ring).

Another embodiment of the present invention is compound or their pharmaceutically acceptable salts of any of the embodiments of Formulae I through V wherein $R^1$ is —C(S)$R^7$ and $R^7$ is alkyl.

Another embodiment of the present invention is compound or their pharmaceutically acceptable salts of any of the embodiments of Formulae I through V wherein $R^1$ is benzoyl which is optionally substituted once or twice by alkyl (e.g., methyl or ethyl), halogen or alkoxy (e.g., methoxy or ethoxy), or haloalkyl (e.g., —CF$_3$).

Another embodiment of the present invention is compound or their pharmaceutically acceptable salts of any of the embodiments of Formulae I through V wherein $R^2$, $R^3$ and $R^4$ are hydrogen.

Another embodiment of the present invention is compounds or their pharmaceutically acceptable salts of any of the embodiment of Formulae I or III above wherein $R^5$ is halogen (e.g., —F or —Cl).

Another embodiment of the present invention is compounds or their pharmaceutically acceptable salts of any of the embodiment of Formulae I, II, or V above wherein $R^6$ is halogen (e.g., —F or —Cl).

Another embodiment of the present invention is compounds or their pharmaceutically acceptable salts of any of the embodiments of Formulae I through IV above wherein $R^{14}$ is H, halogen (e.g., —F or —Cl); —CN; —O$R^7$ (where $R^7$ is H, alkyl (e.g., methyl, ethyl, n-propyl, i-propyl, n-butyl, iso-butyl, sec-butyl, or tert-butyl)); alkyl (e.g., methyl or ethyl) or haloalkyl (e.g., —CF$_3$).

Another embodiment of the present invention is compounds or their pharmaceutically acceptable salts of any of the embodiments of Formulae I through IV above wherein $R^{14}$ is H, alkyl or haloalkyl.

Another embodiment of the present invention is compounds or their pharmaceutically acceptable salts of any of the embodiments of Formulae I through IV above where $R^{13}$ is H, halogen (e.g., —F or —Cl), —CN, alkyl (e.g., methyl, ethyl, n-propyl, i-propyl, n-butyl, iso-butyl, sec-butyl, tert-butyl), —O$R^7$ (where $R^7$ is H, alkyl (e.g., methyl, ethyl, n-propyl, i-propyl, n-butyl, iso-butyl, sec-butyl or tert-butyl) or haloalkyl (e.g., —CF$_3$)), haloalkyl (e.g., —CF$_3$) or phenyl optionally substituted by halogen, —O$R^7$ (where $R^7$ is H, alkyl (e.g., methyl, ethyl, n-propyl, i-propyl, n-butyl, iso-butyl, sec-butyl or tert-butyl) or haloalkyl (e.g., —CF$_3$)) or haloalkyl (e.g., —CF$_3$)).

Another embodiment of the present invention is compounds or their pharmaceutically acceptable salts of any of the embodiments of Formulae I through IV above where $R^{13}$ is H, halogen (e.g., —F or —Cl), —CN, alkyl (e.g., methyl, ethyl, n-propyl, i-propyl, n-butyl, iso-butyl, sec-butyl or tert-butyl), —O$R^7$ (where $R^7$ alkyl, phenyl or phenyl substituted one or twice by halogen, —OH, alkoxy or haloalkoxy), haloalkyl (e.g., —CF$_3$) or phenyl optionally substituted once or twice by halogen (e.g., —F or —Cl) or haloalkyl (e.g., CF$_3$).

Another embodiment of the present invention is compounds or their pharmaceutically acceptable salts thereof of any of the embodiments of Formula I through IV described above where $R^{11}$ is H, alkyl (e.g., methyl or ethyl) or haloalkyl (e.g., —CF$_3$) and $R^{13}$ is H, halogen (e.g., —F or —Cl), —CN, alkyl (e.g., methyl, ethyl, n-propyl, i-propyl, n-butyl, iso-butyl, sec-butyl or tert-butyl), —O$R^7$ (where $R^7$ is H, alkyl (e.g., methyl, ethyl, n-propyl, i-propyl, n-butyl, iso-butyl, sec-butyl, or tert-butyl), or haloalkyl (e.g., —CF$_3$)), haloalkyl (e.g., —CF$_3$) or phenyl optionally substituted by halogen, —O$R^7$ (where $R^7$ is H, alkyl (e.g., methyl, ethyl, n-propyl, i-propyl, n-butyl, iso-butyl, sec-butyl or tert-butyl) or haloalkyl (e.g., —CF$_3$)) or haloalkyl (e.g., —CF$_3$).

Another embodiment of the present invention is compounds or their pharmaceutically acceptable salts thereof of any of the embodiments of Formula I through IV described above where $R^{11}$ is H or alkyl (e.g., methyl or ethyl) and $R^{13}$ is —CN, —C(O)-alkyl (e.g., acetyl), alkoxy (e.g., methoxy or ethoxy), hydroxyl-substituted alkyl or phenyl.

Another embodiment of the present inventions is compounds or their pharmaceutically acceptable salts thereof of any of the embodiments of Formula I through IV described above or their pharmaceutically acceptable salts thereof where $R^{14}$ is H, alkyl (e.g., methyl or ethyl) or haloalkyl (e.g., —CF$_3$) and $R^{13}$ is a group of the formula:

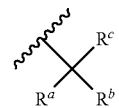

where:
$R^a$ is H, OH, or —C$_1$-C$_3$-alkyl optionally substituted with 1 to 3 —F (e.g. CF$_3$);
$R^b$ is H, —OH, or —C$_1$-C$_3$-alkyl optionally substituted with 1 to 3 —F (e.g. CF$_3$);
$R^c$ is —C$_1$-C$_3$-alkyl optionally substituted with 1 to 3 —F (e.g. CF$_3$), is —OC$_1$-C$_3$-alkyl, —N(H)S(O)$_2$—C$_1$-C$_3$-alkyl, optionally substituted with 1 to 3 —F (e.g. CF$_3$), —N(H)C(O)C$_1$-C$_3$-alkyl, optionally substituted with 1 to 3 —F (e.g. CF$_3$).

Another embodiment of the present invention is compounds or their pharmaceutically acceptable salts of Formula I represented by structural Formula VI

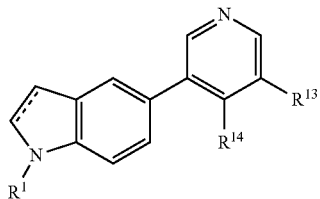

VI wherein R$^1$ is —C(O)R$^7$, —C(S)R$^7$, or benzoyl, which is optionally substituted once or twice by alkyl, halogen, alkoxy or haloalkyl; R$^7$ is alkyl (e.g., methyl or ethyl), haloalkyl, cycloalkyl (e.g. cyclopropyl), phenyl, phenyl substituted once or twice by halogen or alkoxy, or heteroaryl (e.g., thienyl); R$^{13}$ is H, —CN, alkoxy (e.g., methoxy or ethoxy), hydroxy-substituted alkyl, halogen, phenyl or —C(O)-alkyl (e.g., acetyl); and R$^{14}$ is H, alkyl or halogen.

Another embodiment of the present invention is compounds or their pharmaceutically acceptable salts of Formula I represent by Formula VII

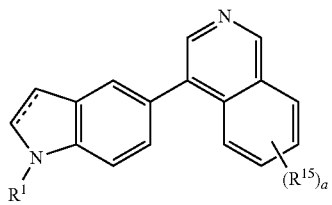

VII wherein R$^1$ is —C(O)R$^7$, —C(S)R$^7$, or benzoyl, which is optionally substituted once or twice by alkyl, halogen, alkoxy or haloalkyl; R$^7$ is alkyl (e.g., methyl or ethyl), haloalkyl, cycloalkyl (e.g. cyclopropyl), phenyl, phenyl substituted once or twice by halogen or alkoxy; a is 0 (i.e., R$^{15}$ is absent), or wherein a is 1 or 2 and R$^{15}$ is alkyl or halo.

Another embodiment of the invention is the following compounds or their pharmaceutically acceptable salts:
1-propanoyl-5-pyridin-3-yl-2,3-dihydro-1H-indole;
1-(3-chloropropanoyl)-5-pyridin-3-yl-2,3-dihydro-1H-indole;
1-(cyclopropylcarbonyl)-5-pyridin-3-yl-2,3-dihydro-1H-indole;
1-[(4-fluorophenyl)carbonyl]-5-pyridin-3-yl-2,3-dihydro-1H-indole1-[(4-fluorophenyl)carbonyl]-5-pyridin-3-yl-2,3-dihydro-1H-indole;
1-[(4-methoxyphenyl)carbonyl]-5-pyridin-3-yl-2,3-dihydro-1H-indole;
1-(penylacetyl)-5-pyridin-3-yl-2,3-dihydro-1H-indole;
5-pyridin-3-yl-1-(thiophen-2-ylcarbonyl)-2,3-dihydro-1H-indole;
4-(1-acetyl-2,3-dihydro-1H-indol-5-yl)isoquinoline;
4-(1-propanoyl-2,3-dihydro-1H-indol-5-yl)isoquinoline;
4-[1-(2-methylpropanoyl)-2,3-dihydro-1H-indol-5-yl]isoquinoline;
4-[1-(cyclopropylcarbonyl)-2,3-dihydro-1H-indol-5-yl]isoquinoline;
1-(5-(pyridin-3-yl)indolin-1-yl)ethanethione;
1-acetyl-5-pyridin-3-yl-1H-indole;
4-(1-acetyl-1H-indol-5-yl)isoquinoline;
1-acetyl-5-(5-fluoropyridin-3-yl)-2,3-dihydro-1H-indole;
5-(1-acetyl-2,3-dihydro-1H-indol-5-yl)pyridine-3-carbonitrile;
1-acetyl-5-(5-methoxypyridin-3-yl)-2,3-dihydro-1H-indole;
1-[5-(1-acetyl-2,3-dihydro-1H-indol-5-yl)pyridin-3-yl]ethanone;
1-[5-(1-acetyl-2,3-dihydro-1H-indol-5-yl)pyridin-3-yl]ethanol;
1-acetyl-5-(5-phenylpyridin-3-yl)-2,3-dihydro-1H-indole; or
1-acetyl-5-(4-methylpyridin-3-yl)-2,3-dihydro-1H-indole.

Another embodiment of the invention is the following compounds or their pharmaceutically acceptable salts:
1-(7-chloro-5-(5-fluoropyridin-3-yl)indolin-1-yl)-2,2,2-trifluoroethanone; or
2,2,2-trifluoro-1-(7-fluoro-5-(5-fluoropyridin-3-yl)indolin-1-yl)ethanone.

As used above, and throughout this disclosure, the following terms, unless otherwise indicated, shall be understood to have the following meanings:

"Mammal" means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Halo" refers to fluorine, chlorine, bromine or iodine radicals. Examples are fluoro, chloro or bromo.

"Halogen" means fluorine, chlorine, bromine, or iodine.

"Haloalkyl" means a halo-alkyl-group in which the alkyl group is as previously described. The bond to the parent moiety is through the alkyl. Non-limiting examples of suitable haloalkyl groups include fluoromethyl, difluoromethyl, —CH$_2$CF$_3$, —CH$_2$CHF$_2$—CH$_2$CH$_2$F, or an alkyl group with one or more terminal carbons tri-substituted with a halogen (e.g., —F) such as, for example —C$_1$-C$_3$alkyl-CF$_3$, —CH(CH$_3$)(CF$_3$), —CH(CF$_3$)$_2$ and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Aryl" means an aromatic monocyclic or multicyclic ring system comprising about 6 to about 14 carbon atoms, preferably about 6 to about 10 carbon atoms. Non-limiting examples of suitable aryl groups include phenyl, naphthyl, indenyl, tetrahydronaphthyl and indanyl.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist protected such as, for example, as an —N(Boc), —N(CBz), —N(Tos) group and the like; such protections are also considered part of this invention. The nitrogen or sulfur atom of the heterocycloalkyl ring can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, oxetanyl, tetrahydrothiophenyl, lactam, lactone, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination, provided that the rings do not include adjacent oxygen and/or sulfur atoms. N-oxides of the ring nitrogens are also included, as well as compounds wherein a ring nitrogen is substituted by an alkyl group to form a quaternary amine. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl (e.g., 1, 5 or 1,7), pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, 7-azaindolyl and the like. The term "heteroaryl" also refers to partially saturated heteroaryl moieties such as, for example, tetrahydroisoquinolyl, tetrahydroquinolyl and the like. All positional isomers are contemplated, e.g., 2-pyridyl, 3-pyridyl and 4-pyridyl.

It should be noted that in heterocycloalkyl ring systems of this invention, there are no hydroxyl groups on carbon atoms adjacent to a N, O or S, as well as there are no N or S groups on carbon adjacent to another heteroatom. Thus, for example, in the ring:

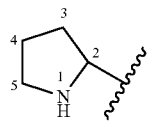

there is no —OH attached directly to carbons marked 2 and 5.

When $R^{13}$ and $R^{14}$ are joined together to form a 5-7 membered carbocyclic ring that is fused to the pyridyl ring to which $R^{13}$ and $R^{14}$ are attached, "carbocyclic" means a cycloalkyl, aryl or partially unsaturated ring composed of 5-7 carbon atoms wherein two of the carbons are shared between the fused rings. When $R^{13}$ and $R^{14}$ are joined together to form a 5-7 membered heterocyclic ring that is fused to the pyridyl ring to which $R^{13}$ and $R^{14}$ are attached, "heterocyclic" means a fully saturated, partially saturated or aromatic ring composed of carbon atoms and one, two or three heteroatoms selected from N, S, or O, wherein two of the carbons are shared between the fused rings. Representative ring include:

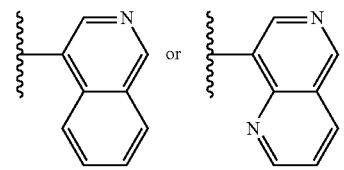 [SMILES: *c1cncc2ccccc12 ; *c1cncc2cccnc12]

When a moiety can be optionally substituted, it means that each carbon and heteroatom (when present) available for substitution in the given moiety may be independently unsubstituted or substituted with specified number of substituents that are the same or different at each occurrence and which result in the creation of a stable structure as is understood to be reasonable by one skilled in the art.

Unless expressly depicted or described otherwise, variables depicted in a structural formula with a "floating" bond, such as $R^{15}$ in structural Formula V, are permitted on any available carbon atom in the ring to which each is attached.

When $R^8$ and $R^9$ or $R^{11}$ and $R^{12}$ together with the nitrogen to which they are attached form a saturated 5- to 7-membered heterocyclic ring, this means a saturated heterocyclic ring composed of, in addition to the one nitrogen atom, carbon atoms and optionally one additional heteroatom selected from N, S or O. Representative examples include:

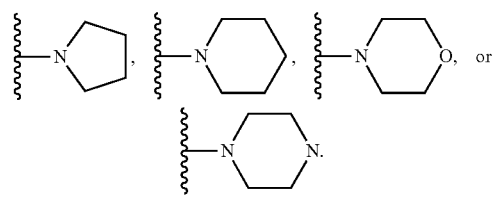

It should also be noted that tautomeric forms such as, for example, the moieties:

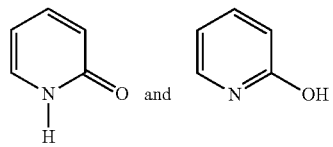 [SMILES: O=c1cccc[nH]1 ; Oc1ccccn1]

are considered equivalent in certain embodiments of this invention.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally, a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I (which includes the compounds of Formulae II-VII) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Compounds of the present invention are effective at inhibiting the synthesis of aldosterone by inhibiting CYP11B2 (aldosterone synthase) and, therefore, might be useful agents for the therapy and prophylaxis of disorders that are associated with elevated aldosterone levels. Accordingly, an object of the instant invention is to provide a method for inhibiting aldosterone synthase, and more particularly selectively inhibiting CYP11B2, in a mammal in need thereof, comprising administering a compound of Formula I to the mammal in an amount effective to inhibit aldosterone synthesis, or more particularly to selectively inhibit CYP11B2, in the mammal. A selective inhibitor of CYP11B2 is intended to mean a compound that preferentially inhibits CYP11B2 as compared to CYP11B1. The inhibition of CYP11B2, as well inhibition of CYP11B1, by the compounds of Formula I can be examined, for example, in the inhibition assays described below.

In general, compounds that have activity as aldosterone synthase inhibitors can be identified as those compounds which have an $IC_{50}$ of less than or equal to about 10 μM; preferably less than or equal to about 250 nM; and most preferably less than or equal to about 100 nM, in the V79-Human-CYP11B2 Assay described below. In general, aldosterone synthase inhibitors that are selective for inhibition of CYP11B2 as compared to CYP11B1 are those that show at least 3-fold greater inhibition for CYP11B2 compared to CYP11B1; preferably at least 20-fold inhibition for CYP11B2 compared to CYP11B1; and more preferably at least 100-fold greater inhibition for CYP11B2 compared to CYP11B1, in the V79-Human-CYP11B2 Assay as compared to the V79-Human-CYP11B1 Assay.

Due to their ability to inhibit CYP11B2, the compounds of the present invention may be useful to treat and/or ameliorate the risk for hypertension, hypokalemia, renal failure (e.g., chromic renal failure), restenosis, Syndrome X, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, heart failure (e.g., congestive heart failure), diastolic heart failure, left ventricle diastolic dysfunction, diastolic heart failure, systolic dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening or necrosis of coronary arteries.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 30 mg/kg, preferably 0.001 to 20 mg/kg, in particular 0.01 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 1.5 mg, 2 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The term "preventing" or "prevention" as used herein refers to administering a compound before the onset of clinical symptoms.

It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the compound may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting aldosterone synthase, inhibiting CYP11B2, for normalizing a disturbed aldosterone balance, or for treating or preventing any of the medical conditions described herein, in dosage amounts described herein.

The amount of active compound of Formula I and its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

Since the compounds of Formula I inhibit aldosterone synthase, apart from use as pharmaceutically active compounds in human medicine and veterinary medicine, they can also be employed as a scientific tool or as aid for biochemical investigations in which such an effect on aldosterone synthase and aldosterone levels is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents (or therapeutic agents) may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to the following pharmaceutically acceptable salts, metabolites, solvates, prodrugs, or polymorphs thereof: angiotensin converting enzyme (ACE) inhibitors (e.g, alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists (e.g., candesartan, eprosartan, irbesartan, losartan, olmesartan, telmisartan, valsartan) neutral endopeptidase inhibitors (e.g., thiorphan and phosphoramidon), aldosterone antagonists, renin inhibitors (e.g. enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, bepridil, diltiazem, felodipine, gallopamil, nicardipine, nifedipine, niludipine, nimodipine, nisoldipine veraparmil), potassium channel activators (e.g., nicorandil, pinacidil, cromakalim, minoxidil, aprilkalim, loprazolam), diuretics (e.g., hydrochlorothiazide); including loop diuretics such as ethacrynic acid, furosemide, bumetanide and torsemide, sympatholitics, beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, metformin, rosiglitazone), dipeptidyl peptidase 4 inhibitors (e.g., sitagliptin, alogliptin, vildagliptin, saxagliptin, linagliptin, dutogliptin, and gemigliptin); or with other drugs beneficial for the prevention or the treatment of the above-mentioned diseases including nitroprusside and diazoxide.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods and one skilled in the art would have resources such as *Chemical Abstracts* or *Beilstein* at his or her disposal to assist in devising an alternative method of preparing a specific compound.

The compounds of the present invention can be prepared according to the procedures of the following Schemes using appropriate materials and are further exemplified by the specific Examples which follow. Moreover, by utilizing the procedures described herein, one of ordinary skill in the art can readily prepare additional compounds of the present invention claimed herein.

Throughout the synthetic schemes, abbreviations are used with the following meanings unless otherwise indicated: AcCN=acetonitrile; aq=aqueous, Ar=aryl; BSA=bovine serum albumin; Bu=butyl, t-Bu=tert-butyl; n-BuLi=n-butyllithium; conc, conc.=concentrated; DMAP=4-dimethylaminopyridine; DME=dimethyl ether; DCM=dichloromethane; DMEM=Dulbecco's modified eagle medium; DMF=N,N-dimethylformamide; eq.=equivalent(s); EDTA=ethylenediaminetetraacetic acid; Et=ethyl; EtOAc=ethyl acetate; EtOH=ethanol; FBS=Fetal Bovine Serum; h, hr=hour; HPLC=High pressure liquid chromatography; HTRF=homogenous time resolved fluorescence; i-PrOH=isopropanol; i-Pr=isopropyl; LCMS=liquid chromatography-mass spectroscopy; Me=methyl; MeOH=methanol; min, min.=minute; MS=mass spectroscopy; NCS=N-Chlorosuccinimide; NMR=nuclear magnetic resonance; PBS=phosphate buffered saline; Pd/C=palladium on activated carbon; Ph=phenyl; Pr=propyl; Py=pyridyl; OAc=acetate; RT, rt=room temperature; sat.=saturated; TEA=triethylamine; TFA=trifluroracetic acid; THF=tetrahydrofuran.

As will be known to those skilled in the art, in all schemes, the products of Formula I and all synthetic intermediates may be purified from unwanted side products, reagents and solvents by recrystallization, trituration, preparative thin layer chromatography, flash chromatography on silica gel as described by W. C. Still et al, J. Org. Chem. 1978, 43, 2923, or reverse-phase HPLC. Compounds purified by HPLC may be isolated as the corresponding salt.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chomatography using a homochiral stationary phase and, in the case of cis/trans isomers and diastereomers, normal-phase and reverse-phase chromatography.

Chemical reactions were monitored by LCMS, and the purity and identity of the reaction products were assayed by LCMS (electrospray ionization) and NMR. Data for $^1$H NMR are reported with chemical shift ($\delta$ ppm), multiplicity (s=singlet, d=doublet, t=triplet, q=quartet, m=multiplet, br s=broad singlet, br m=broad multiplet), coupling constant (Hz), and integration. Unless otherwise noted, all LCMS ions listed are [M+H]. All temperatures are degrees Celsius unless otherwise noted.

The following examples are provided so that the invention might be more fully understood. They should neither be construed as forming the only genus that is considered as the invention nor limiting the invention in any way.

Example 1

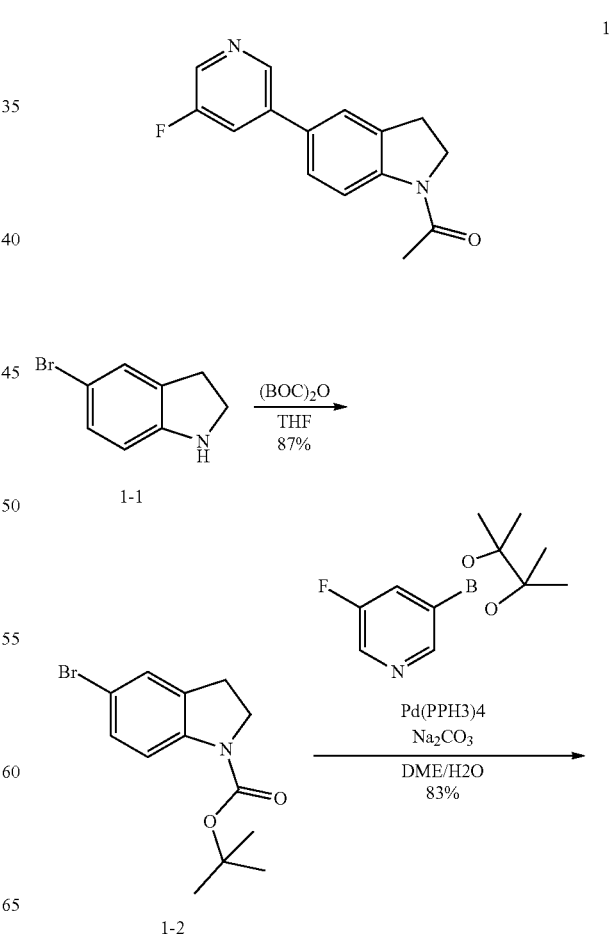

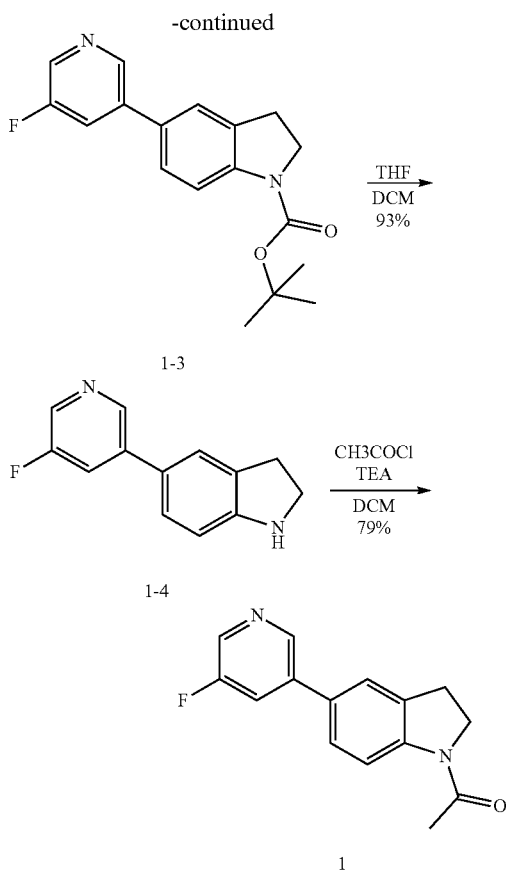

Step A tert-butyl 5 bromoindoline-1-carboxylate

BOC$_2$O (9.70 g, 44.4 mmol) was added to solution of commercially available 5-bromoindoline (8 g, 40.4 mmol) in THF (20 mL) and the mixture was stirred at room temperature overnight. The solvent was evaporated and the crude was chromatographed on a Biotage 65i column eluting with hexane/ethyl acetate (0-100%, 1.7 L) to give the title compound. $^1$H NMR (500 MHz, CHCl$_3$-d): δ 7.74 (s, 1H), 7.28 (m 2H), 3.99 (m, 2H), 3.10 (m, 2H), 1.59 (s, 9H), MS (M+1) 299.

Step B tert-butyl 5-(5-fluoropridine-3-yl)indolin-1-carboxylate

To a stirred solution of 5 bromoindoline-1-carboxylate (1.0 g, 3.35 mmol), 3-fluoro-5-(4,4,5,5-tetramethyl-1,3,2-dioxaborolan-2-yl)pyridine (0.89 g, 4.0 mmol), in DME/H$_2$O (3:1, 12 mL) was added Pd(PPh$_3$)$_4$ (0.194 g, 0.17 mol), and Na$_2$CO$_3$ (1.60 g, 15.1 mmol). The mixture was degassed, flushed with nitrogen and stirred at 80° C. for 2 h. The mixture was cooled to room temperature and diluted with ethyl acetate (30 mL). The organic layer was washed with water (30 mL), brine (30 ml), dried (Na$_2$SO$_4$), filtered and the solvent was evaporated. The residue was chromatographed on a biotage 45M column eluting with hexane/ethyl acetate (0-100%, 1.2 L) to give the title compound. $^1$H NMR (500 MHz, CHCl$_3$-d): δ 8.66 (m, 1H), 8.42 (m, 1H), 7.96 (m, 1H), 7.55-7.45 (m, 1H), 7.43-7.36 (m, 2H), 4.06 (m, 2H), 3.19 (m, 2H), 1.65 (s, 9H), MS (M+1) 315.

Step C 5-(5-fluoropyridin-3-yl)indoline

TFA (5 mL) was added to a solution of tert-butyl 5-(5-fluoropridine-3-yl)indolin-1-carboxylate (1-3, 860 g, 2.74 mmol) in methylene chloride (5 mL) at 0° C. and the mixture was stirred at room temperature overnight. The reaction mixture was diluted with methylene chloride (50 mL) and washed with saturated NaHCO$_3$ (30 mL), water (30 mL) and brine (30 mL), dried over Na$_2$SO$_4$, filtered and evaporated. The crude product was chromatographed on a Biotage 45M column eluting with hexane/ethyl acetate (0-100%, 1.4 L) to give the title compound. $^1$H NMR (500 MHz, CHCl$_3$-d): δ 8.64 (s, 1H), 8.37 (d, 1H), 7.54 (dt, 1H), 7.37 (s, 1H), 7.26 (m, 1H), 6.74 (d, 1H), 3.67 (t, 2H), 3.14 (t, 2H), MS (M+1) 215.

Step D 1-(5-(5-fluoropyridin-3-yl)indolin-1-yl)ethanone

To a solution of 5-(5-fluoropyridin-3-yl)indoline (1-4 0.040 g, 0.187 mmol) in methylene chloride (5 mL), TEA (0.078 mL, 0.56 mmol) and acetyl chloride (0.030 g, 0.373 mmol) were added to the reaction mixture. The reaction mixture was stirred at room temperature for 1 h. The solvent was evaporated and the crude was purified by reverse phase Gilson (SunFire™ C18 column, eluting with water/AcCN 5-40% in 12 min.) to give the title compound. $^1$H NMR (500 MHz, CDCl$_3$): δ 8.67 (s, 1H); 8.44 (s, 1H); 8.33 (d, J=8.3 Hz, 1H); 7.61 (d, J=9.5 Hz, 1H); 7.46-7.41 (m, 2H); 4.24-4.11 (m, 2H); 3.39-3.27 (m, 2H); 2.49 (s, 1H); 2.29 (s, 3H), MS (M+1) 257.

The compounds in Table 1 were all prepared using the chemistry described in Example 1, step B.

TABLE 1

| Ex | Structure | IUPAC Name | MS (M + 1) | H$^1$ NMR 500 MHz, CDCl$_3$ |
|---|---|---|---|---|
| 2 | 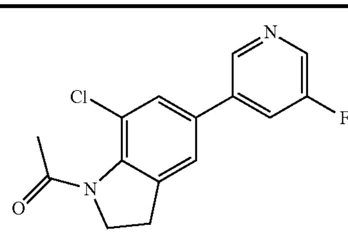 | 1-(7-chloro-5-(5-fluoropyridine-3-yl)indolin-1-yl)ethanone | 291.17 | δ 9.78 (s, 1 H); 9.62 (s, 1 H); 8.74 (d, J = 9.3 Hz, 1 H); 8.58 (s, 1 H); 8.51 (s, 1 H); 5.41-5.35 (m, 2 H); 4.29 (t, J = 7.6 Hz, 2 H); 3.48 (s, 3 H) |

TABLE 1-continued

| Ex | Structure | IUPAC Name | MS (M + 1) | H¹ NMR 500 MHz, CDCl₃ |
|---|---|---|---|---|
| 3 | 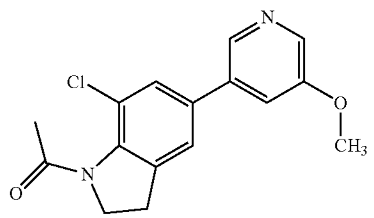 [SMILES: COc1cncc(-c2cc(Cl)c3c(c2)CCN3C(C)=O)c1] | 1-(7-chloro-5-(5-methoxypyridin-3-yl)indolin-1-yl)ethanone | 303.13 | δ 9.70 (s, 1 H); 9.52 (s, 1 H); 8.85 (s, 1 H); 8.57 (s, 1 H); 8.51 (s, 1 H); 5.38-5.33 (m, 2 H); 5.15 (s, 3 H); 4.31-4.25 (m, 2 H); 3.46 (s, 3 H) |
| 4 | 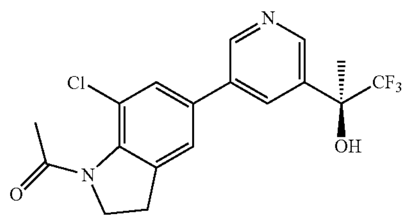 | (S)-1-(7-chloro-5-(5-(1,1,1,-trifluoro-2-hydroxypropan-2-yl)pydine-3-yl)indolin-1-yl)ethanone | 385.07 | δ 8.89 (s, 1 H); 8.85 (s, 1 H); 8.34 (s, 1 H); 7.42 (d, J = 13.6 Hz, 2 H); 5.72 (bs, 1 H); 4.28-4.22 (m, 2 H); 3.20-3.14 (m, 2 H); 2.36 (d, J = 2.1 Hz, 3 H); 1.93 (s, 3 H) |
| 5 | 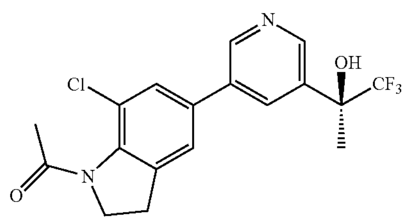 | (R)-1-(7-chloro-5-(5-(1,1,1,-trifluoro-2hydroxypropan-2-yl)pyridine-3-yl)indolin-1-yl)ethanone | 385.07 | δ 8.79 (d, J = 13.6 Hz, 2 H); 8.18 (s, 1 H); 7.45 (s, 1 H); 7.40 (s, 1 H); 4.28-4.21 (m, 2 H); 3.16 (t, J = 7.6 Hz, 2 H); 2.35 (s, 3 H); 1.91 (s, 3 H |
| 6 | 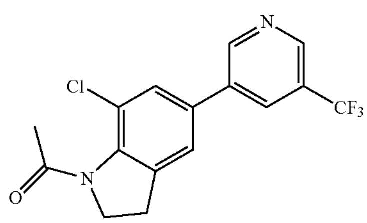 [SMILES: CC(=O)N1CCc2cc(-c3cncc(C(F)(F)F)c3)cc(Cl)c21] | 1-(7-chloro-5-(5-(triuoromethyl)pyridine-3-yl)indolin-1-yl)ethanone | 341 | δ 9.00 (d, J = 2.1 Hz, 1 H); 8.90 (s, 1 H); 8.07 (s, 1 H); 7.49 (s, 1 H); 7.47-7.39 (m, 1 H); 4.30-4.23 (m, 2 H); 3.18 (t, J = 7.6 Hz, 2 H); 2.36 (s, 3 H) |
| 7 | 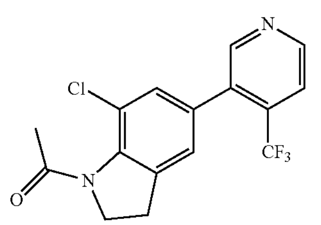 [SMILES: CC(=O)N1CCc2cc(-c3cnccc3C(F)(F)F)cc(Cl)c21] | 1-(7-chloro-5-(4-(trifluoromethyl)pyridine-3-yl)indolin-1-yl)ethanone | 341 | δ 9.89 (bs, 1 H); 9.67 (bs, 1 H); 8.36 (m, 1 H); 8.26 (m, 1 H); 8.16 (m, 1 H); 5.35-5.30 (m, 2 H); 4.25-4.20 (m, 2 H); 3.43 (s, 9 H) |
| 8 | 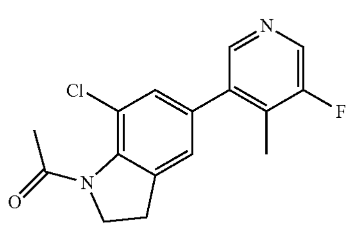 [SMILES: CC(=O)N1CCc2cc(-c3cncc(F)c3C)cc(Cl)c21] | 1-(7-chloro-5-(5-fluoro-4-methylpyridin-3-yl)indolin-1-yl)ethanone | 312.14 | 8.42 (s, 1 H); 8.29 (s, 1 H); 7.21 (s, 1 H); 7.12 (s, 1 H); 4.26 (t, J = 7.5 Hz, 2 H); 3.15 (t, J = 7.6 Hz, 2 H); 2.37 (s, 3 H); 2.29 (d, J = 2.2 Hz, 3 H) |
| 9 | 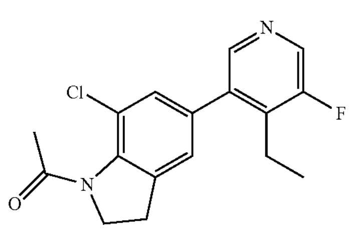 [SMILES: CCc1c(F)cncc1-c1cc(Cl)c2c(c1)CCN2C(C)=O] | 1-(7-chloro-5-(4-ethyl-5-fluoropyridin-3-yl)indolin-1-yl)ethanone | 319.11 | δ 8.42 (s, 1 H); 8.27 (s, 1 H); 7.21 (s, 1 H); 7.11 (s, 1 H); 4.27 (t, J = 7.6 Hz, 2 H); 3.16 (t, J = 7.6 Hz, 2 H); 2.70 (q, J = 7.6 Hz, 2 H); 2.37 (s, 3 H); 1.17 (t, J = 7.5 Hz, 3 H) |

TABLE 1-continued

| Ex | Structure | IUPAC Name | MS (M + 1) | H¹ NMR 500 MHz, CDCl₃ |
|---|---|---|---|---|
| 10 | 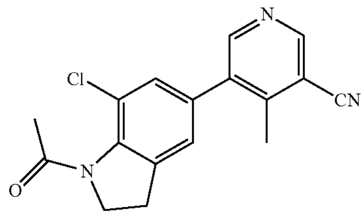 [SMILES: CC(=O)N1CCc2cc(-c3cncc(C#N)c3C)cc(Cl)c21] | 5-(1-acetyl-7-chloroindolin-5-yl)-4-methylnicotinotrile | 312.10 | δ 8.84-8.75 (m, 1 H); 8.63-8.58 (m, 1 H); 7.20 (s, 1 H); 7.10 (s, 1 H); 4.27 (t, J = 7.6 Hz, 2 H); 3.17 (t, J = 7.6 Hz, 2 H); 2.54 (s, 3 H); 2.37 (s, 3 H) |
| 11 | 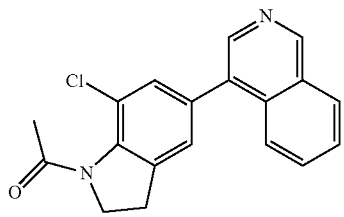 [SMILES: CC(=O)N1CCc2cc(-c3cncc4ccccc34)cc(Cl)c21] | 1-(7-chloro-5-(isoquinolin-4-yl)indolin-1-yl)ethanone | 323.09 | 9.30 (s, 1 H); 8.49 (s, 1 H); 8.09 (d, J = 8.1 Hz, 1 H); 7.94 (d, J = 8.5 Hz, 1 H); 7.78-7.67 (m, 2 H); 7.41 (s, 1 H); 7.35-7.24 (m, 1 H); 4.30 (t, J = 7.5 Hz, 2 H); 3.18 (t, J = 7.5 Hz, 2 H) |
| 12 | 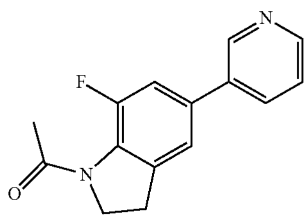 [SMILES: CC(=O)N1CCc2cc(-c3cccnc3)cc(F)c21] | 1-(7-fluoro-5-(pyridine-3-yl)indolin-1-yl)ethanone | 257.10 | δ 9.08 (s, 1 H); 8.75 (d, J = 5.2 Hz, 1 H); 8.34 (d, J = 8.0 Hz, 1 H); 7.83 (dd, J = 8.1, 5.2 Hz, 1 H); 7.36 (s, 1 H); 7.28 (m, 1H); 4.32-4.24 (m, 2 H); 3.23-3.17 (m, 2 H); 2.35 (d, J = 4.2 Hz, 3 H) |
| 13 | 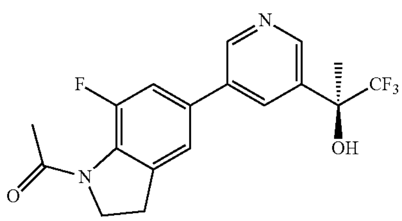 | (S)-1-(7-fluoro-5-(5-(1,1,1-trifluoro-2-hydroxypropan-2-yl)pyridin-3-yl)indolin-1-yl)ethanone | 369.10 | δ 9.07-8.99 (m, 1 H); 8.97 (s, 1 H); 8.55 (s, 1 H); 7.36 (s, 1 H); 7.29 (m, 1H); 4.32-4.25 (m, 2 H); 3.78 (bs, 1H); 3.26-3.20 (m, 2 H); 2.37 (d, J = 3.9 Hz, 3 H); 1.99 (s, 3 H) |
| 14 | 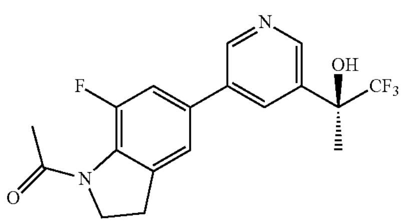 | (R)-1-(7-fluoro-5-(5-(1,1,1-trifluoro-2-hydroxypropan-2-yl)pyridin-3-yl)indolin-1-l)ethanone | 369.12 | δ 9.03-8.94 (m, 1 H); 8.92 (s, 1 H); 8.46 (m, 1 H); 7.35 (s, 1 H); 7.28 (m, 1H); 4.32-4.26 (m, 2 H); 3.22 (m, 2 H); 2.36 (d, J = 3.9 Hz, 3 H); 1.98 (s, 3 H) |
| 15 | 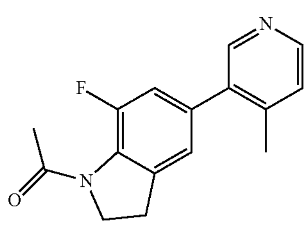 [SMILES: CC(=O)N1CCc2cc(-c3cnccc3C)cc(F)c21] | 1-(7-fluoro-5-(4-methylpyridin-3-yl)indolin-1-yl)ethanone | 272.12 | 8.71-8.61 (m, 2 H); 7.68 (d, J = 5.7 Hz, 1 H); 7.06-6.95 (m, 2 H); 4.31-4.24 (m, 2 H); 3.21-3.14 (m, 2 H); 2.56 (s, 3 H); 2.35 (d, J = 4.0 Hz, 3 H) |
| 16 | 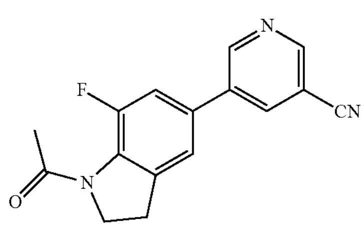 [SMILES: CC(=O)N1CCc2cc(-c3cncc(C#N)c3)cc(F)c21] | 5-(1-acetyl-7-fluoroindolin-5-yl)nicotinonitrile | 282.10 | δ 9.02 (s, 1 H); 8.89 (s, 1 H); 8.13-8.11 (m, 1 H); 7.29 (s, 1 H); 7.23 (m, 1H); 4.31-4.24 (m, 2 H); 3.22-3.15 (m, 2 H); 2.35 (d, J = 4.4 Hz, 3 H) |

TABLE 1-continued

| Ex | Structure | IUPAC Name | MS (M + 1) | H¹ NMR 500 MHz, CDCl₃ |
|---|---|---|---|---|
| 17 | 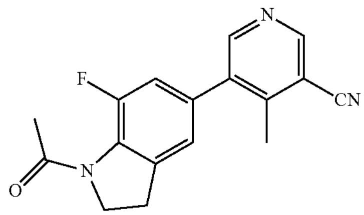 [SMILES: CC(=O)N1CCc2cc(-c3cncc(C#N)c3C)cc(F)c21] | 5-(1-acetyl-7-fluoroindolin-5-yl)-4-methylnicotinonitrile | 296.12 | δ 8.92-8.76 (m, 1 H); 8.62 (s, 1 H); 7.03-6.91 (m, 2 H); 4.31-4.24 (m, 2 H); 3.20-3.13 (m, 2 H); 2.55 (s, 3 H); 2.36 (d, J = 4.2 Hz, 3 H) |
| 18 | 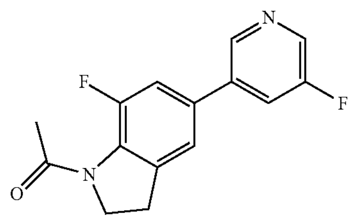 [SMILES: CC(=O)N1CCc2cc(-c3cncc(F)c3)cc(F)c21] | 1-(7-fluoro-5-(5-fluoropyridine-3-yl)indolin-1-yl)-ethanone | 275.10 | δ 8.68 (s, 1 H); 8.50 (s, 1 H); 7.65-7.61 (m, 1 H); 7.30 (d, J = 2.6 Hz, 1 H); 7.24 (m, 1H); 4.31-4.24 (m, 2 H); 3.21-3.14 (m, 2 H); 2.35 (d, J = 4.4 Hz, 3 H) |
| 19 | 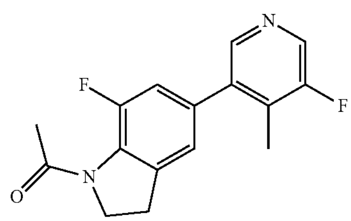 [SMILES: CC(=O)N1CCc2cc(-c3cncc(F)c3C)cc(F)c21] | 1-(7-fluoro-5-(5-fluoro-4-methylpyridine-3-yl)indolin-1-yl)-ethanone | 289.11 | δ 8.50 (s, 1 H); 8.41 (s, 1 H); 7.06-6.95 (m, 2 H); 4.32-4.25 (m, 2 H); 3.21-3.14 (m, 2 H); 2.40-2.35 (m, 6 H) |
| 20 | 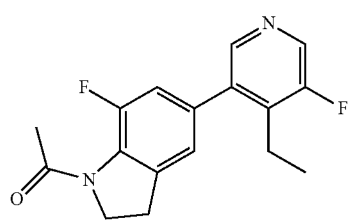 [SMILES: CCc1c(F)cncc1-c1cc(F)c2c(c1)CCN2C(C)=O] | 1-(5-(4-ethyl-5-fluoropyridine-3-yl)-7-fluoroindolin-1-yl)ethanone | 303.13 | δ 8.51 (s, 1 H); 8.38 (s, 1 H); 7.04-6.93 (m, 2 H); 4.33-4.25 (m, 2 H); 3.21-3.14 (m, 2 H); 2.79 (dd, J = 15.0, 7.5 Hz, 2 H); 2.37 (d, J = 4.1 Hz, 3 H); 1.25-1.17 (m, 3 H) |
| 21 | 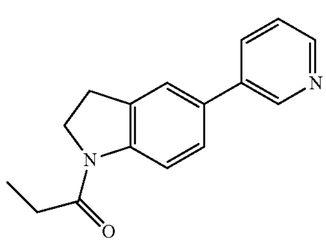 [SMILES: CCC(=O)N1CCc2cc(-c3cccnc3)ccc21] | 1-propanoyl-5-pyridin-3-yl-2,3-dihydro-1H-indole | 253.13 | δ 1.26 (t, J = 7.3 Hz, 3H), 2.48 (q, J = 7.3 Hz, 2H), 3.28 (t, J = 8.3 Hz, 2H), 4.11 (t, J = 8.3 Hz, 2H), 7.33 (dd, J = 4.9, 7.8 Hz, 1H), 7.41 (d, J = 3.4 Hz, 1H), 7.42 (s, 1H), 7.84 (dt, J = 2.0, 7.8 Hz, 1H), 8.34 (d, J = 8.0 Hz, 1H), 8.55 (d, J = 4.0 Hz,1H), 8.82 (d, J = 2.2 Hz, 1H) |
| 22 | 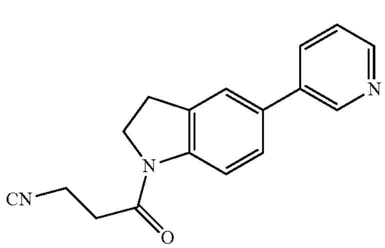 | 1-(3-chloro-propanoyl)-5-pyridin-3-yl-2,3-dihydro-1H-indole | 287.35 | δ 2.95 (t, J = 6.8 Hz, 2H), 3.30 (t, J = 8.5 Hz, 2H), 3.93 (t, J = 6.8 Hz, 2H), 4.15 (t, J = 8.5 Hz, 2H), 7.34 (dd, J = 4.8, 7.8 Hz, 1H), 7.44 (m, 2H), 7.84 (dt, J = 1.9, 7.8 Hz, 1H), 8.31 (d, J = 8.2 Hz, 1H), 8.56 (d, J = 4.5 Hz,1H), 8.82 (d, J = 1.9 Hz, 1H). |

TABLE 1-continued

| Ex | Structure | IUPAC Name | MS (M + 1) | H¹ NMR 500 MHz, CDCl₃ |
|---|---|---|---|---|
| 23 | 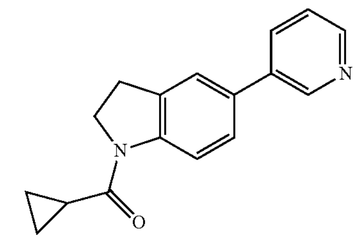 [SMILES: O=C(C1CC1)N1CCc2cc(-c3cccnc3)ccc21] | 1-(cyclopropyl-carbonyl)-5-pyridin-3-yl-2,3-dihydro-1H-indole | 265.66 | δ 0.91 (m, 2H), 1.15 (m, 2H), 1.78 (s, br, 1H), 3.30 (t, J = 8.3 Hz, 2H), 4.33 (t, J = 8.3 Hz, 2H), 7.34 (dd, J = 4.8, 7.8 Hz, 1H), 7.40 (m, 2H), 7.85 (dt, J = 2.0, 7.8 Hz, 1H), 8.26 (s, br, 1H), 8.55 (d, J = 4.6 Hz,1H), 8.82 (d, J = 1.8 Hz, 1H). |
| 24 | 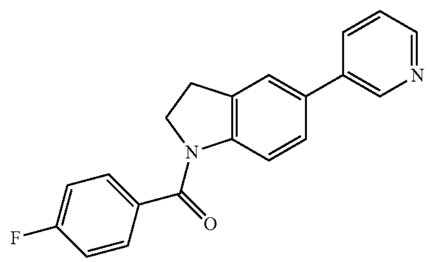 [SMILES: O=C(c1ccc(F)cc1)N1CCc2cc(-c3cccnc3)ccc21] | 1-[(4-fluorophenyl)carbonyl]-5-pyridin-3-yl-2,3-dihydro-1H-indole | 319.23 | δ 3.16 (t, J = 8.3 Hz, 2H), 4.07 (t, J = 8.3 Hz, 2H), 7.34 (m, 2H), 7.46 (dd, J = 4.8, 8.0 Hz, 1H), 7.56 (s, br, 1H), 7.67 (d, J = 0.9 Hz,1H), 7.70 (m, 2H ), 8.05 (d, J = 8.0 Hz, 1H), 8.53 (dd, J = 1.5, 4.7 Hz, 1H), 8.87 (d, J = 1.8 Hz, 1H). |
| 25 | 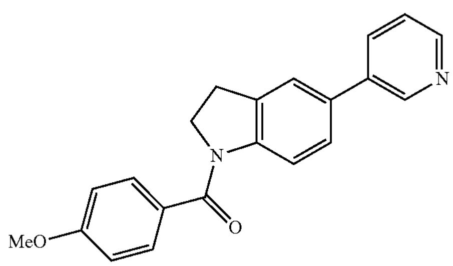 [SMILES: COc1ccc(C(=O)N2CCc3cc(-c4cccnc4)ccc32)cc1] | 1-[(4-methoxyphenyl)carbonyl]-5-pyridin-3-yl-2,3-dihydro-1H-indole | 331.36 | δ 3.16 (t, J = 8.3 Hz, 2H), 3.83 (s, 3H), 4.11 (t, J = 8.3 Hz, 2H), 7.04 (m, 2H), 7.45 (dd, J = 4.8, 7.9 Hz, 1H), 7.54 (d, J = 7.7 Hz, 1H) 7.60 (m, 2H), 7.66, (s, 1H), 8.04 (dt, J = 2.0, 8.0 Hz, 1H), 8.52 (dd, J = 1.5, 4.7 Hz, 1H), 8.87 (d, J = 2.0 Hz, 1H). |
| 26 | 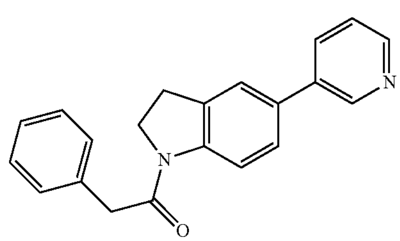 [SMILES: O=C(Cc1ccccc1)N1CCc2cc(-c3cccnc3)ccc21] | 1-(Phenylacetyl)-5-pyridin-3-yl-2,3-dihydro-1H-indole | 315.66 | δ 3.24 (t, J = 8.5 Hz, 2H), 3.84 (s, 2H), 4.13 (t, J = 8.5 Hz, 2H), 7.28 (m, 1H), 7.34 (m, 5H), 7.39 (s, 1H), 7.42 (d, J = 8.5 Hz,1H), 7.83 (dt, J = 1.8, 7.9 Hz, 1H), 8.36 (d, J = 8.4 Hz, 1H), 8.55 (d, J = 1.3, 4.7 Hz, 1H), 8.81 (d, J = 2.1 Hz, 1H). |
| 27 | 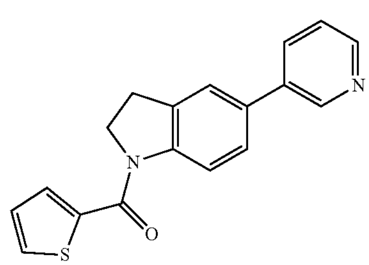 [SMILES: O=C(c1cccs1)N1CCc2cc(-c3cccnc3)ccc21] | 5-Pyridin-3-yl-1-(thiophen-2-ylcarbonyl)-2,3-dihydro-1H-indole | 307.57 | δ 3.30 (t, J = 8.3 Hz, 2H), 4.45 (t, J = 8.3 Hz, 2H), 7.13 (t, J = 8.3 Hz, 1H), 7.34 (dd, J = 4.8, 7.9 Hz, 1H), 7.44 (m, 2H), 7.56 (dd, J = 0.9, 5.0 Hz, 1H), 7.62 (dd, J = 0.8, 3.7 Hz, 1H), 7.83 (dt, J = 2.0, 7.9 Hz, 1H), 8.18 (s, br, 1H), 8.56 (dd, J = 1.5, 4.8 Hz, 1H), 8.83 (d, J = 2.0 Hz, 1H). |

TABLE 1-continued

| Ex | Structure | IUPAC Name | MS (M + 1) | H¹ NMR 500 MHz, CDCl₃ |
|----|-----------|------------|------------|------------------------|
| 28 | 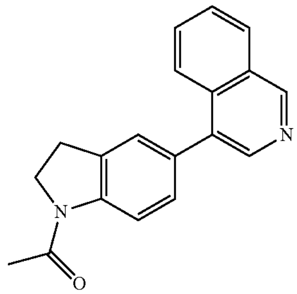 [SMILES: CC(=O)N1CCc2cc(-c3cncc4ccccc34)ccc21] | 4-(1-acetyl-2,3-dihydro-1H-indol-5-yl)isoquinoline | 289.46 | δ 2.28 (s, 3H), 3.30 (t, J = 8.4 Hz, 2H), 4.16 (t, J = 8.4 Hz, 2H), 7.32 (s, 1H), 7.35 (d, J = 8.2 Hz, 1H), 7.62 (t, J = 7.4 Hz, 1H), 7.67 (t, J = 7.4 Hz, 1H), 7.93 (d, ³J = 8.4 Hz, 1H), 8.03 (d, J = 7.9 Hz, 1H), 8.35 (d, J = 8.2 Hz, 1H), 8.46 (s, 1H), 9.24 (s, 1H). |
| 29 | 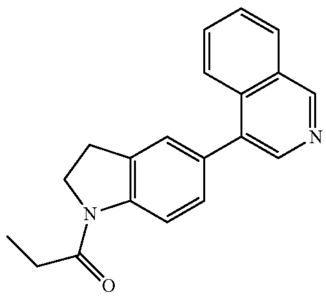 [SMILES: CCC(=O)N1CCc2cc(-c3cncc4ccccc34)ccc21] | 4-(1-propanoyl-2,3-dihydro-1H-indol-5-yl)isoquinoline | 303.57 | δ 1.28 (t, J = 7.3 Hz, 3H), 2.51 (q, J = 7.3 Hz, 2H), 3.30 (t, J = 8.4 Hz, 2H), 4.14 (t, J = 8.4 Hz, 2H), 7.32 (s, 1H), 7.35 (d, J = 8.3 Hz, 1H), 7.62 (t, J = 7.3 Hz, 1H), 7.67 (t, J = 7.3 Hz, 1H), 7.93 (d, J = 8.4 Hz, 1H), 8.03 (d, J = 8.0 Hz, 1H), 8.39 (t, J = 8.1 Hz, 1H), 8.46 (s, 1H), 9.23 (s, 1H). |
| 30 | 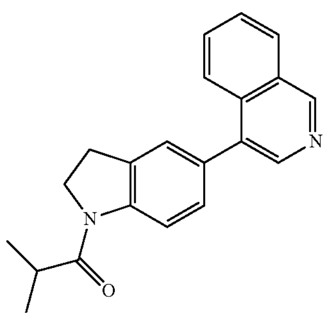 [SMILES: CC(C)C(=O)N1CCc2cc(-c3cncc4ccccc34)ccc21] | 4-[1-(2-methyl-propanoyl)-2,3-dihydro-1H-indol-5-yl]isoquinoline | 315.36 | δ 1.28 (d, J = 6.7 Hz, 6H), 2.84 (m, 1H), 3.31 (t, J = 7.9 Hz, 2H), 4.24 (t, J = 8.5 Hz, 2H), 7.35 (m, 2H), 7.66 (m, 1H), 7.72 (m, 1H), 7.97 (d, J = 8.1 Hz, 1H), 8.07 (d, J = 7.8 Hz, 1H), 8.42 (s, J = 7.8 Hz, 1H), 8.47 (s, 1H), 9.26 (s, 1H). |
| 31 | 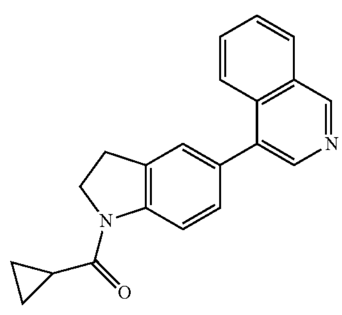 [SMILES: O=C(C1CC1)N1CCc2cc(-c3cncc4ccccc34)ccc21] | 4-[1-(cyclopropyl-carbonyl)-2,3-dihydro-1H-indol-5-yl]isoquinoline | 315.36 | δ 0.93 (m, 2H), 1.17 (m, 2H), 1.81 (s, br, 1H), 3.33 (s, br, 2H), 4.37 (s, br, 2H), 7.34 (m, 2H), 7.62-7.70 (m 2H), 7.94 (d, J = 8.1 Hz, 1H), 8.04 (d, J = 7.7 Hz, 1H), 8.32 (s, br, 1H), 8.47 (s, 1H), 9.24 (s, 1H). |
| 32 | 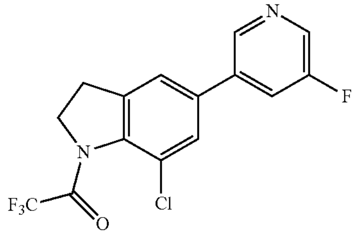 [SMILES: O=C(N1CCc2cc(-c3cncc(F)c3)cc(Cl)c21)C(F)(F)F] | 1-(7-chloro-5-(5-fluoropyridin-3-yl)indon-1-yl)-2,2,2-trifluoroethanone | 385.59 | δ 3.41 (t, J = 7.6 Hz, 2H), 4.41(t, J = 7.6 Hz, 2H), 7.70-7.71(m, 1H), 7.76-7.77(m,1H), 7.94-7.97(m, 1H), 8.51-8.52(d, J = 2.8 Hz, 1H), 8.79(t, J = 1.6 Hz,1H) |

TABLE 1-continued

| Ex | Structure | IUPAC Name | MS (M + 1) | H¹ NMR 500 MHz, CDCl₃ |
|---|---|---|---|---|
| 33 | 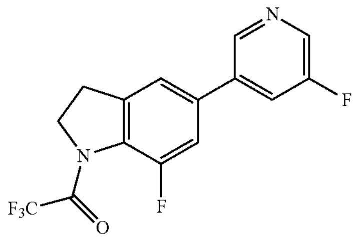 [SMILES: O=C(N1CCc2cc(-c3cncc(F)c3)cc(F)c21)C(F)(F)F] | 2,2,2-trifluoro-1-(7-fluoro-5-(5-fluoropyridin-3-yl)indolin-1-yl)ethanone | 369.68 | δ 3.42 (d, J = 7.7 Hz, 2H), 4.43 (td, J = 7.8 Hz, J = 0.9 Hz, 2H), 7.62-7.66 (m, 1H), 7.92-7.98 (m, 1H), 8.52 (d, J = 2.8 Hz, 1H), 8.80 (t, J = 2.0 Hz, 1H). |
| 34 | 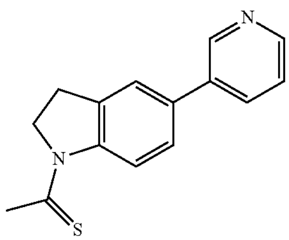 [SMILES: CC(=S)N1CCc2cc(-c3cccnc3)ccc21] | 1-(5-(pyridin-3-yl)indolin-1-yl)ethanethione | 255.32 | δ 2.75 (s, 3H), 2.99 (s, 3H), 3.18 (t, J = 8.2Hz, 2H), 4.42 (t, J = 8.2Hz, 2H), 4.46 (t, J = 8.2Hz, 2H), 7.47-7.50 (m, 2H), 8.10-8.12 (m, 2H), 8.55-8.57 (m, 2H), 9.52 (d, J = 8.2 Hz, 1H) |

Example 35

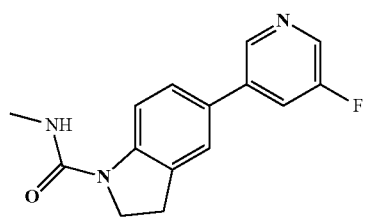

36

TEA (0.078 mL, 0.56 mmol) and isocyanatomethane (0.021 g, 0.373 mmol) were added to a solution of 5-(5-fluoropyridin-3-yl)indoline (0.040 g, 0.187 mmol) in methylene chloride (5 mL). The mixture was stirred at room temperature for 1 h. The solvent was evaporated and the crude was purified by reverse phase Gilson (SunFire™ C18 column, eluting with water/AcCN 5-40% in 12 min.) to yield 5-(5-fluoropyridin-3-yl)-N-methylindoline-1-carboxamide. ¹H NMR (500 MHz, CDCl₃): δ 8.66 (s, 1H); 8.42 (s, 1H); 8.06 (d, J=8.4 Hz, 1H); 7.57 (dt, J=9.8, 2.2 Hz, 1H); 7.46-7.38 (m, 2H); 4.65 (d, J=5.6 Hz, 1H); 3.99 (t, J=8.7 Hz, 2H); 3.29 (t, J=8.7 Hz, 2H); 2.96 (d, J=4.6 Hz, 3H), MS (M+1) 272.

The compounds in Table 2 were all prepared using the chemistry described in Example 35

TABLE 2

| Ex | Structure | IUPAC Name | MS (M + 1) | H¹ NMR 500 MHz, CDCl₃ |
|---|---|---|---|---|
| 36 | 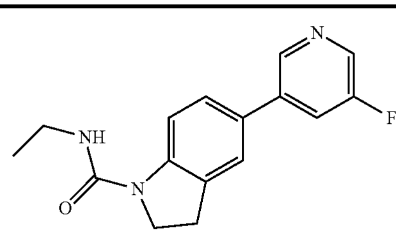 | N-ethyl-5-(5-fluoropyridin-3-yl)indoline-1-carboxamide | 286 | δ 8.67 (s, 1 H); 8.42 (s, 1 H); 8.06 (d, J = 8.4 Hz, 1 H); 7.59 (d, J = 9.7 Hz, 1 H); 7.44-7.36 (m, 2 H); 4.65 (s, 1 H); 3.99 (t, J = 8.7 Hz, 2 H); 3.45-3.39 (m, 2 H); 3.31-3.24 (m, 2 H); 1.29-1.19 (m, 3 H) |
| 37 | 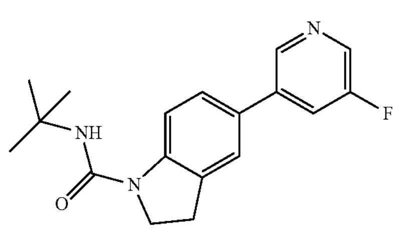 [SMILES: CC(C)(C)NC(=O)N1CCc2cc(-c3cncc(F)c3)ccc21] | N-(tert-butyl)5-(5-fluoropyridin-3-yl)indolin-1-carboxamide | 313 | δ 8.67 (s, 1 H); 8.42 (s, 1 H); 8.01 (d, J = 8.4 Hz, 1 H); 7.61 (d, J = 9.6 Hz, 1 H); 7.43-7.36 (m, 2 H); 4.49 (s, 1 H); 3.99-3.92 (m, 2 H); 3.29-3.22 (m, 2 H); 1.46-1.46 (m, 9H) |

TABLE 2-continued

| Ex | Structure | IUPAC Name | MS (M + 1) | H¹ NMR 500 MHz, CDCl₃ |
|---|---|---|---|---|
| 38 | 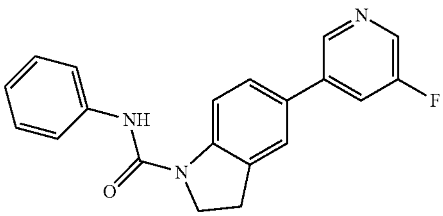 [SMILES: O=C(Nc1ccccc1)N1CCc2cc(-c3cncc(F)c3)ccc21] | 5-(5-fluoropyridin-3-yl)-N-phenylindoline-1-carboxamide | 335.3 | δ 8.68 (s, 1 H); 8.44 (s, 1 H); 8.09 (d, J = 8.3 Hz, 1 H); 7.61 (d, J = 9.6 Hz, 1 H); 7.56-7.40 (m, 5 H); 7.40-7.23 (m, 2 H); 6.59 (s, 1 H); 4.19-4.11 (m, 2 H); 3.37-3.29 (m, 2 H) |
| 39 | 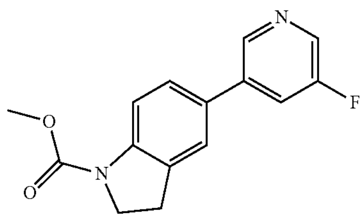 [SMILES: COC(=O)N1CCc2cc(-c3cncc(F)c3)ccc21] | methyl 5-(5-fluoropyridin-3-yl)indoline-1-carboxylate | 273.4 | δ 8.68 (s, 1 H); 8.45 (s, 1 H); 8.00 (s, 1 H); 7.60 (d, J = 9.6 Hz, 1 H); 7.47-7.38 (m, 2 H); 4.11 (bs, 2 H); 3.89 (bs, 2H); 3.26-3.19 (m, 3H) |
| 40 | 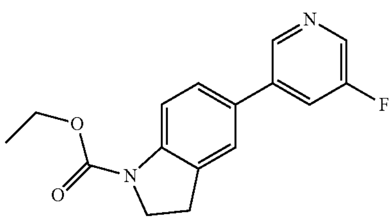 [SMILES: CCOC(=O)N1CCc2cc(-c3cncc(F)c3)ccc21] | ethyl 5-(5-fluoropyridin-3-yl)indoline-1-carboxylate | 287 | δ 8.68 (s, 1 H); 8.44 (s, 1H); 8.00 (s, 1 H); 7.61 (d, J = 9.6 Hz, 1 H); 7.47-7.39 (m, 2 H); 4.34 (bs, 2 H); 4.15-4.08 (m, 2 H); 3.26-3.19 (m, 2 H); 1.40 (m, 3 H) |
| 41 | 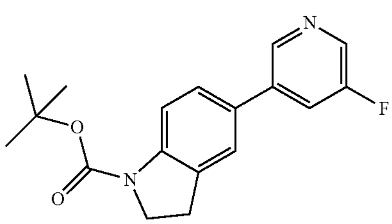 [SMILES: CC(C)(C)OC(=O)N1CCc2cc(-c3cncc(F)c3)ccc21] | tert-butyl 5-(5fluoropyridin-3-yl)indoline-1-carboxylate | 315 | δ 8.67 (s, 1 H); 8.43 (s, 1 H); 7.97 (s, 1 H); 7.60 (d, J = 9.8 Hz, 1 H); 7.44-7.37 (m, 2 H); 4.27-3.87 (m, 2 H); 3.23-3.15 (m, 2 H); 1.60 (s, 9H) |
| 42 | 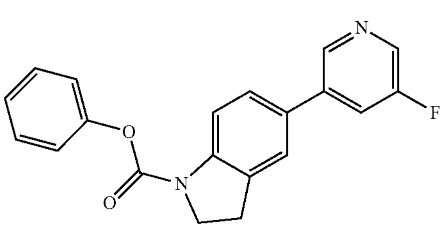 [SMILES: O=C(Oc1ccccc1)N1CCc2cc(-c3cncc(F)c3)ccc21] | phenyl 5-(5-fluoropyridin-3-yl)indoline-1-carboxylate | 335.3 | δ 8.69 (s, 1 H); 8.46 (s, 1 H); 8.02 (d, J = 8.1 Hz, 1 H); 7.63 (d, J = 9.5 Hz, 1 H); 7.48-7.42 (m, 5 H); 7.29-7.24 (m, 2 H); 4.35 (m, 2 H); 3.33 (m, 2 H) |

Example 43

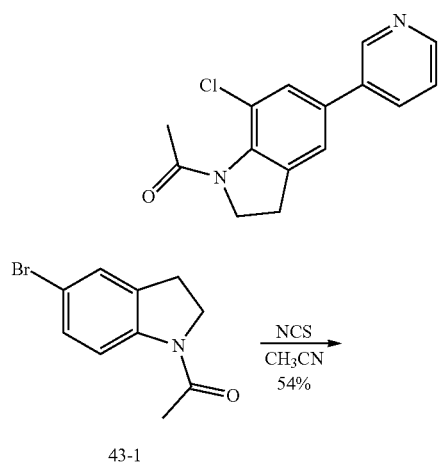

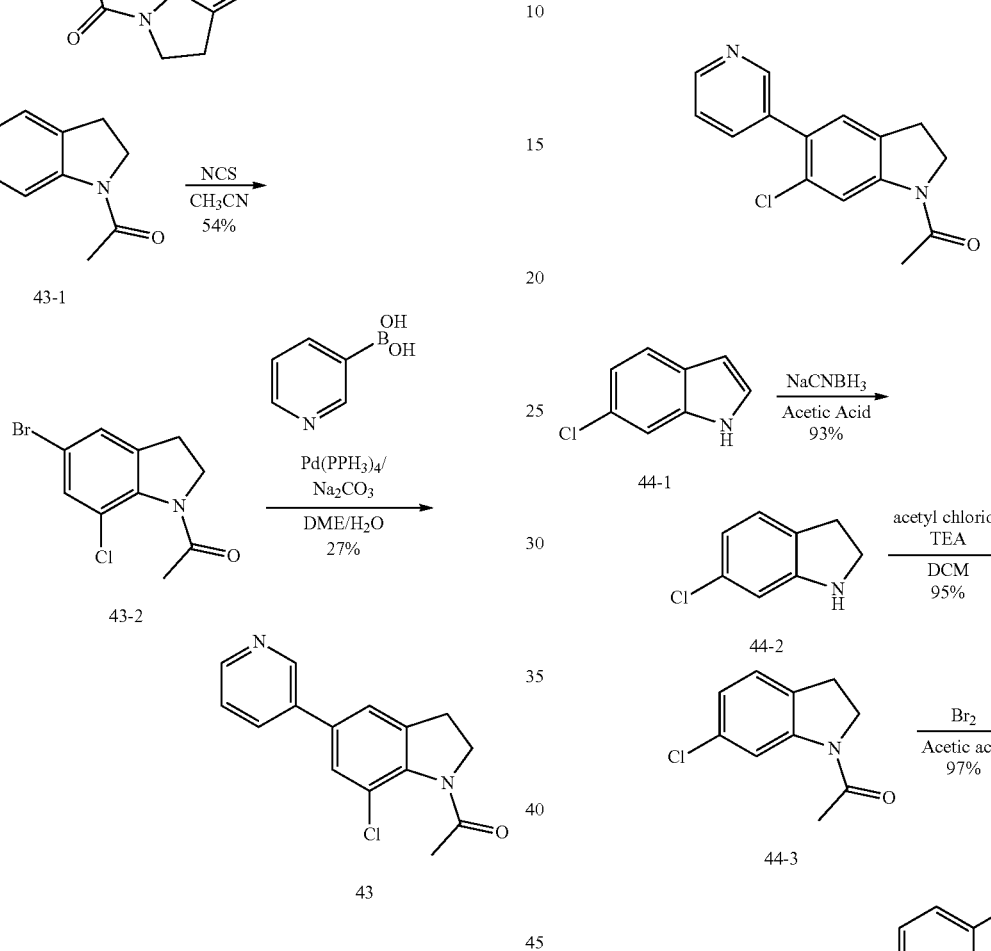

Step A 1-(5-bromo-7-chloroindolin-1-yl)ethanone

A mixture of commercially available 1-acetyl-5-bromoindoline (43-1, 7.0 g, 29.2 mmol) and NCS (4.28 g, 32.1 mmol) in 300 mL of acetonitrile was heated under reflux for 24 h. The reaction mixture was cooled to room temperature and the solvent was removed under reduced pressure. The residue was chromatography on a Biotage 65i column eluting with hexane/ethyl acetate (0-5-%) to give the title compound. $^1$H NMR (500 MHz, CDCl$_3$): δ 7.45 (s, 0H); 7.29 (s, 1H); 4.19 (t, J=7.6 Hz, 2H); 3.10-3.03 (m, 2H); 2.30 (s, 3H), MS (M+1) 275.5.

Step B: 1-(7-chloro-5-(pyridin-3-yl)indolin-1-yl) ethanone

The title compound was prepared according to the procedure of Example 1 step B using 1-(5-bromo-7-chloroindolin-1-yl)ethanone in place of bromoindoline-1-carboxylate as the starting material. The product was purified by reverse phase Gilson (SunFire™ C18 column, eluting with water/AcCN 5-50% in 12 min. to give the title compound. $^1$H NMR (500 MHz, CDCl$_3$): δ 10.16 (s, 1H); 9.89 (s, 1H); 9.53 (s, 1H); 9.33 (d, J=7.8 Hz, 1H); 8.85 (s, 1H); 8.64 (s, 1H); 5.45-5.38 (m, 2H); 4.37-4.31 (m, 2H); 3.56-3.48 (m, 3H). MS (M+1) 273.

Example 44

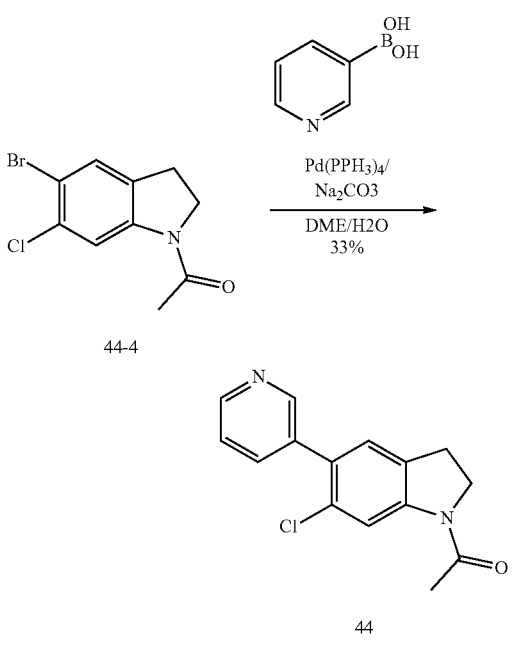

Step A 6-chloroindoline

To a stirred solution of 6-chloro-1H-indole (5 g, 33.0 mmol) in glacial acetic acid (93 ml) at 15° C. under an atmosphere of nitrogen was added in one portion sodium cyanoborohydride (6.22 g, 99 mmol). The mixture was stirred at 15° C. for 2 h. Water (500 mL) was added and the mixture was cooled in an ice bath and slowly made strongly basic with sodium hydroxide pallets. The mixture was extracted with ether (4×200 mL). The ether extracts were washed with water (400 ml), brine (400 mL) dried over anhydrous potassium carbonate, and concentrated in vacuo to give the title compound. $^1$H NMR (500 MHz, CDCl$_3$): δ 7.02 (d, J=7.8 Hz, 1H); 6.68 (dd, J=7.8, 1.9 Hz, 1H); 6.62 (d, J=1.9 Hz, 1H); 3.61 (t, J=8.4 Hz, 2H); 3.54 (s, 1H); 3.01 (t, J=8.4 Hz, 2H), MS (M+1) 14.3.

Step B 1-(6-chloroindolin-1-yl)ethanone

To a stirred solution of 6-chloroindoline (44-1, 4.0 g, 26.0 mmol) at 0° C. in methylene chloride (25 mL) was added TEA (14.5 mL, 104 mmol) and acetyl chloride (4.1 g, 53 mmol). The mixture was stirred to room temperature (1 h) and diluted with methylene chloride (100 ml). The organic layer was washed with saturated aqueous NaHCO$_3$ (2×50 mL), water (50 mL), brine (50 ml) dried (MgSO$_4$), filtered and the solvent was evaporated under reduced pressure to give the title compound. $^1$H NMR (500 MHz, CDCl$_3$): δ 8.25 (s, 1H); 7.08 (d, J=7.9 Hz, 1H); 6.99 (d, J=8.0 Hz, 1H); 4.13-4.05 (m, 2H); 3.21-3.07 (m, 2H); 2.23 (s, 3H), MS (M+1) 180.17.

Step C 1-(5-bromo-6-chloroindolin-1-yl)ethanone

To a stirred solution of 1-(6-chloroindolin-1-yl)ethanone (44-2, 4.2 g, 21.4 mmol) in acetic acid (200 mL) at 0° C. was added bromine (1.1 mL, 21.4 mmol). The mixture was stirred to room temperature (4 h) and the product (ppt.) was filtered off to give the title compound. $^1$H NMR (500 MHz, CDCl$_3$): δ 8.31 (s, 1H); 7.35 (s, 1H); 4.08 (t, J=8.5 Hz, 2H); 3.19-3.12 (m, 2H); 2.22 (s, 3H), MS (M+1) 275.2.

Step D 1-(6-chloro-5-(pyridin-3-yl)indoline-1-yl)ethanone

The title compound was prepared according to the procedure of Example 1 step B using 1-(5-bromo-6-chloroindolin-1-yl)ethanone in place of bromoindoline-1-carboxylate as the starting material. The product was purified by reverse phase Gilson (SunFire™ C18 column, eluting with water/AcCN 5-50% in 12 min. to give the title compound. $^1$H NMR (500 MHz, CDCl$_3$): δ 8.92 (s, 1H); 8.81 (d, J=5.6 Hz, 1H); 8.45 (s, 1H); 8.06 (bs, 1H); 7.89 (t, J=6.8 Hz, 1H); 7.21 (s, 1H); 4.24-4.16 (m, 2H); 3.32-3.25 (m, 2H); 2.31 (s, 3H), MS (M+1) 273.03

The compounds in Table 3 were prepared using the chemistry described in Example 44.

TABLE 3

| Ex | Structure | IUPAC Name | MS (M + 1) | H$^1$ NMR 500 MHz, CDCl$_3$ |
|---|---|---|---|---|
| 45 | 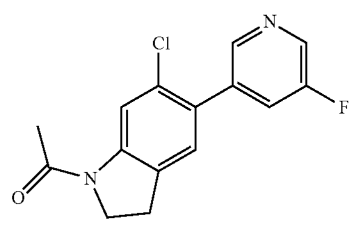 [SMILES: CC(=O)N1CCc2cc(-c3cncc(F)c3)c(Cl)cc21] | 1-(6-chloro-5-(5-fluoropyridine-3-yl)indolin-1-yl)ethanone | 291.07 | δ 8.55 (m, 2 H); 8.43 (s, 1 H); 7.77 (d, J = 8.8 Hz, 1 H); 7.17 (s, 1 H); 4.22-4.14 (m, 2 H); 3.30-3.23 (m, 2 H); 2.30 (s, 3 H) |
| 46 | 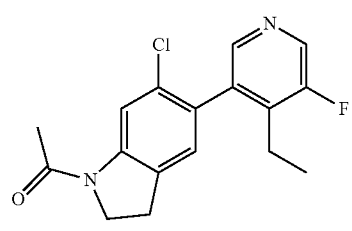 [SMILES: CCc1c(F)cncc1-c1cc2c(cc1Cl)N(C(C)=O)CC2] | 1-(6-chloro-5-(4-ethyl-5-fluoropyridine-3-yl)indolin-1-yl)ethanone | 319.10 | δ 8.55 (s, 1 H); 8.31 (s, 1 H); 7.68 (m, 1 H); 7.51 (m, 1 H); 4.23-4.07 (m, 2 H); 3.30-3.23 (m, 2 H); 2.78-2.68 (m, 1 H); 2.61-2.51 (m, 1 H); 2.30 (s, 3 H); 1.09 (t, J = 7.4 Hz, 3 H) |
| 47 | 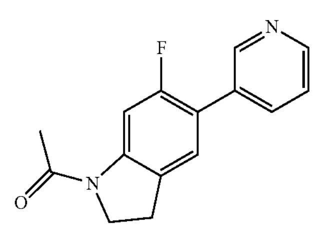 [SMILES: CC(=O)N1CCc2cc(-c3cccnc3)c(F)cc21] | 1-(6-fluoro-5-(pyridin-3-yl)indon-1-yl)ethanone | 257.11 | δ 8.93 (s, 1 H); 8.68 (s, 1 H); 8.26 (s, 1 H); 8.13 (d, J = 12.4 Hz, 1 H); 7.69 (m , 1 H); 7.28 (m, 1H); 4.20 (t, J = 8.4 Hz, 2 H); 3.31-3.24 (m, 2 H); 2.29 (s, 2 H) |

TABLE 3-continued

| Ex | Structure | IUPAC Name | MS (M + 1) | H¹ NMR 500 MHz, CDCl₃ |
|---|---|---|---|---|
| 48 | 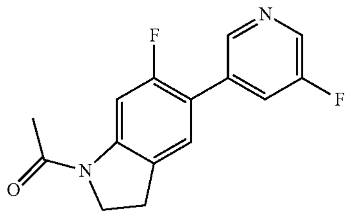 [SMILES: CC(=O)N1CCc2cc(-c3cncc(F)c3)c(F)cc21] | 1-(6-fluoro-5-(5-fluoropyridin-3-yl)indolin-1-yl)ethanone | 275.10 | δ 8.66 (s, 1 H); 8.50 (s, 1 H); 8.12 (d, J = 12.4 Hz, 1 H); 7.80 (d, J = 9.2 Hz, 1 H); 7.27 (m, 1H); 4.19 (t, J = 8.4 Hz, 2 H); 3.31-3.24 (m, 2 H); 2.29 (s, 3 H) |
| 49 | 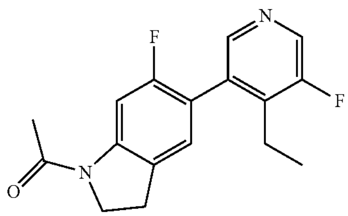 [SMILES: CCc1c(F)cncc1-c1cc2c(cc1F)N(C(C)=O)CC2] | 1-(5-(4-ethyl-5-fluoropyridin-3-yl)-6-fluoroindolin-1-yl)ethanone | 303.13 | δ 8.54 (s, 1 H); 8.39 (s, 1 H); 8.13 (d, J = 11.1 Hz, 1 H); 7.04 (d, J = 7.0 Hz, 1 H); 4.21 (t, J = 8.4 Hz, 2 H); 3.31-3.24 (m, 2 H); 2.72 (d, J = 8.6 Hz, 2 H); 2.31 (s, 3 H); 1.16-1.07 (m, 3 H) |

Example 50

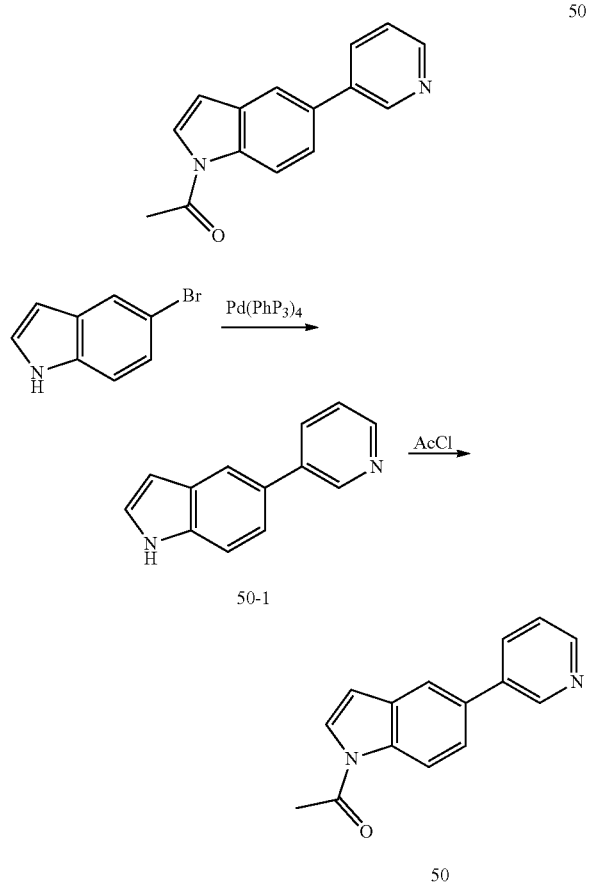

Step A 5-(pyridin-3-yl)-1H-indole

A suspension of 5-bromoindole (250 mg, 1.26 mmol), pyridin-3-ylboronic acid (186 mg, 1.51 mmol), sodium carbonate (667 mg, 6.30 mmol) and tetrakis(triphenylphosphine)palladium (0) (73 mg, 0.06 mmol) in dimethoxyethane (30 mL) and water (10 mL) was stirred at 90° C. under nitrogen for 2 h. The reaction mixture was cooled to room temperature slowly and then diluted with water. The aqueous layer was extracted with EtOAc and the combined organic layers were washed with brine twice and dried over MgSO₄. After evaporation in vacuo, the resulting residue was purified by flash chromatography on silica gel (EtOAc/n-hexane, 1:100 to 1:2) to yield a pale yellow solid. ¹H-NMR (500 MHz, CDCl₃): δ 7.37 (ddd, J=0.8, 4.8, 7.9 Hz, 1H), 7.41 (m, 1H), 7.49 (m, 2H), 7.59 (m, 2H), 7.88 (dt, J=2.0, 7.9 Hz, 1H), 8.60 (dd, J=1.6, 4.8 Hz, 1H), 8.86 (dd, J=0.6, 2.4 Hz, 1H).

Step B 1-Acetyl-5-pyridin-3-yl-1H-indole

To a stirred solution of 50-1 (163 mg, 0.84 mmol) in 1,2-dichloroethane (6 mL) was added triethylamine (0.17 ml, 1.26 mmol), acetic anhydride (0.30 ml, 3.28 mmol) and DMAP (20 mg, 0.16 mmol) in sequence under N₂. The solution was heated to 60° C. for 8 h. Upon cooling to ambient temperature, the reaction was diluted with EtOAc (6 mL) and washed with a saturated solution of ammonium chloride, and the aqueous layer was extracted with EtOAc (3×10 mL). The combined organic layers were dried over MgSO₄ and concentrated in vacuo. The crude product was purified by flash column chromatography on silica gel (EtOAc/n-hexane, 1:50 to 1:2) to give pale yellow crystals. mp 138-140° C., R$_f$=0.16 (EtOAc/n-hexane, 1:1). ¹H-NMR (500 MHz, CDCl₃): δ 2.67 (s, 3H), 6.71 (d, J=3.8 Hz, 1H), 7.38 (dd, J=4.8, 7.9 Hz, 1H), 7.48 (d, J=3.7 Hz, 1H), 7.57 (dd, J=1.8, 8.5 Hz, 1H), 7.77 (d, J=1.7 Hz, 1H), 7.93 (dt, J=1.8, 7.9 Hz, 1H), 8.54 (d, J=8.5 Hz, 1H), 8.59 (dd, J=1.5, 4.8 Hz, 1H), 8.90 (d, J=1.8 Hz, 1H). ¹³C-NMR (125 MHz, CDCl₃): δ 23.9, 109.2, 117.1, 119.4, 123.6, 124.4, 126.1, 131.1, 133.4, 134.7, 135.4, 137.0, 148.0, 148.3, 168.5. MS (ESI) m/z=237.36 [M+H]⁺.

The compounds in Table 4 were prepared using the chemistry described in Example 50.

TABLE 4

| Ex | Structure | IUPAC Name | MS (M + 1) | H¹ NMR 500 MHz, CDCl₃ |
|---|---|---|---|---|
| 51 | 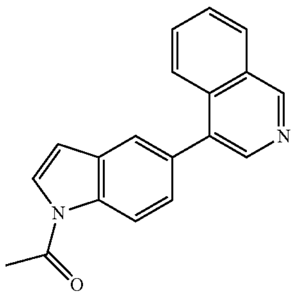 [SMILES: CC(=O)n1ccc2cc(-c3cncc4ccccc34)ccc21] | 4-(1-acetyl-1H-indol-5-yl)isoquinoline | 287.57 | δ 2.70 (s, 3H), 6.73 (d, J = 3.7 Hz, 1H), 7.51 (dd, J = 1.7, 8.5 Hz, 1H), 7.53 (d, J = 3.7 Hz, 1H), 7.66 (m, 2H), 7.70 (d, J = 1.4 Hz, 1H), 7.94 (d, J = 8.4 Hz, 1H), 8.06 (dd, J = 1.3, 7.4 Hz, 1H), 8.54 (s, 1H), 8.59 (d, J = 8.4 Hz, 1H), 9.28 (s, 1H) |

Example 52

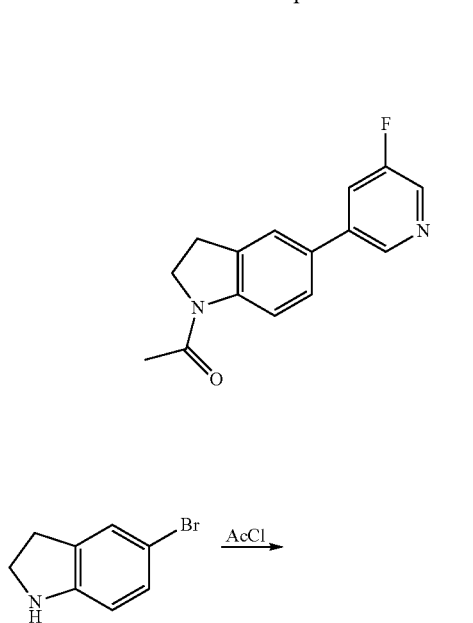

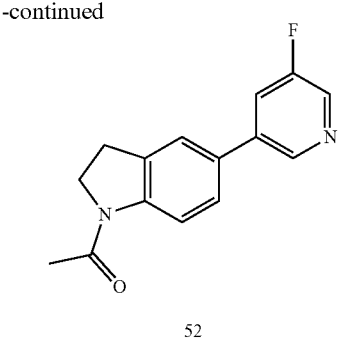

Step A 1-Acetyl-5-bromo-2,3-dihydro-1H-indole

The title compound were synthesized using 5-bromoindoline (1.80 g, 9.09 mmol), acyl chloride (0.62 mL, 10.9 mmol), pyridine (1.10 mL, 13.6 mmol) and anhydrous THF (35 mL) to yield the crude product as grey solids. The crude product was used directly to next step without further purification.

Step B 1-[5-(4,4,5,5-Tetramethyl-[1,3,2]dioxaborolan-2-yl)-2,3-dihydro-indol-1-yl]-ethanone To a solution of 52-1 (1.86 g, 7.75 mmol) in dioxane (31 mL) was added bis(pinacolato)diboron (3.93 g, 15.5 mmol), Pd(dPPf)₂Cl₂ (0.57 g, 0.78 mmol) and anhydrous potassium acetate (3.80 g, 38.7 mmol) under N₂. The reaction was heated at 105° C. for 2 h. Upon cooling to room temperature, water (20 mL) was added to dilute, and the resulting mixture was extracted with EtOAc (3×15 mL). The combined organic layers were washed with brine, dried over MgSO₄ and concentrated in vacuo. The crude product was purified by flash column chromatography on silica gel (EtOAc/n-hexane, 1:50 to 1:2) to yield a pale yellow solid. ¹H-NMR (500 MHz, CDCl₃): δ 1.34 (s, 12H), 2.32 (s, 3H), 3.18 (t, J=8.4 Hz, 2H), 4.05 (t, J=8.5 Hz, 2H), 7.62 (s, 1H), 7.67 (d, J=8.0 Hz, 1H), 8.19 (d, J=8.1 Hz, 1H).

Step C 1-Acetyl-5-(5-fluoropyridin-3-yl)-2,3-dihydro-1H-indole

A suspension of 52-2 (150 mg, 0.52 mmol), 3-bromo-5-fluoropyridine (111 mg, 0.63 mmol), sodium carbonate (277 mg, 2.61 mmol) and tetrakis(triphenylphosphine) palladium (0) (30 mg, 0.03 mmol) in dimethoxyethane (9 mL) and water (3 mL) was stirred at 90° C. under nitrogen for 2 h. The reaction mixture was cooled to room temperature slowly and then diluted with water. The aqueous layer was extracted with EtOAc and the combined organic layers were washed with brine twice and dried over MgSO$_4$. After evaporation in vacuo, the resulting residue was purified by flash chromatography on silica gel (MeOH/CH$_2$Cl$_2$, 0 to 2%) and crystallization from acetone to yield colorless crystals. mp 178-180° C., R$_f$=0.26 (MeOH/CH$_2$Cl$_2$, 1:20). $^1$H-NMR (500 MHz, CDCl$_3$): δ 2.26 (s, 3H), 3.28 (t, J=8.4 Hz, 2H), 4.13 (t, J=8.5 Hz, 2H), 7.40 (m, 2H), 7.56 (dt, J=2.0, 9.6 Hz, 1H), 8.30 (d, J=8.2 Hz, 1H), 8.41 (d, J=1.8 Hz, 1H), 8.64 (s, 1H). $^{13}$C-NMR (125 MHz, CDCl$_3$): δ 24.2, 27.9, 49.0, 117.4, 118.1, 120.7 (d, $^2J_{C,F}$=18.6 Hz), 123.2, 126.8, 131.5, 132.3, 136.0 (d, $^2J_{C,F}$=23.3 Hz), 138.1 (d, $^4J_{C,F}$=3.6 Hz), 143.6 (d, $^4J_{C,F}$=3.2 Hz), 159.7 (d, $^1J_{C,F}$=257 Hz), 168.9. MS (ESI) m/z=257.76 [M+H]$^+$.

The compounds in Table 5 were prepared using the chemistry described in Example 52.

TABLE 5

| Ex | Structure | IUPAC Name | MS (M + 1) | H$^1$ NMR 500 MHz, CDCl$_3$ |
|---|---|---|---|---|
| 53 | 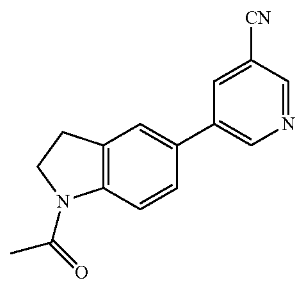 [SMILES: CC(=O)N1CCc2cc(-c3cncc(C#N)c3)ccc21] | 5-(1-acetyl-2,3-dihydro-1H-indol-5-yl)pyridine-3-carbonitrile | 264.83 | δ 2.27 (s, 3H), 3.30 (t, J = 8.4 Hz, 2H), 4.15 (t, J = 8.5 Hz, 2H), 7.40 (m, 2H), 8.10 (t, J = 2.1 Hz, 1H), 8.34 (d, J = 8.3 Hz, 1H), 8.80 (d, J = 1.5 Hz, 1H), 9.00 (d, J = 2.2 Hz, 1H). |
| 54 | 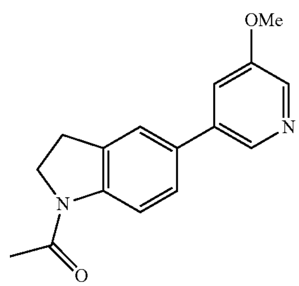 [SMILES: COc1cncc(-c2ccc3c(c2)CCN3C(C)=O)c1] | 1-acetyl-5-(5-methoxypyridin-3-yl)-2,3-dihydro-1H-indole | 269.37 | δ 2.25 (s, 3H), 3.27 (t, J = 8.5 Hz, 2H), 3.92 (s, 3H), 4.12 (t, J = 8.5 Hz, 2H), 7.35 (t, J = 2.1 Hz,1H), 7.40 (m, 2H), 8.26 (d, J = 2.6 Hz,1H), 8.29 (d, J = 8.3 Hz,1H), 8.43 (d, J = 1.8 Hz,1H). |
| 55 | 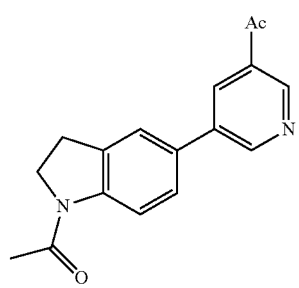 [SMILES: CC(=O)c1cncc(-c2ccc3c(c2)CCN3C(C)=O)c1] | 1-[5-(1-acetyl-2,3-dihydro-1H-indol-5-yl)pyridin-3-yl]ethanone | 281.67 | δ 2.26 (s, 3H), 2.69 (s, 3H), 3.29 (t, J = 8.5 Hz, 2H), 4.13 (t, J = 8.5 Hz, 2H), 7.45 (m, 2H), 8.32 (t, J = 8.3 Hz,1H), 8.38 (t, J = 2.1 Hz,1H), 8.98 (d, J = 2.0 Hz,1H), 9.01 (s, 1H). |
| 56 | 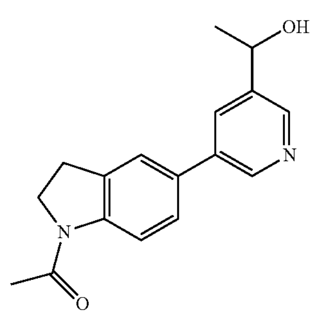 [SMILES: CC(=O)N1CCc2cc(-c3cncc(C(C)O)c3)ccc21] | 1-[5-(1-acetyl-2,3-dihydro-1H-indol-5-yl)pyridin-3-yl]ethanol | 283.77 | δ 1.53 (s, J = 6.5 Hz, 3H), 2.67 (s, 3H), 3.29 (d, J = 5.3 Hz, 2H), 4.19 (d, J = 3.8 Hz, 2H), 4.98 (q, J = 6.5 Hz, 1H), 7.49 (s, 1H), 7.55 (s, 1H), 8.05 (s, 1H), 8.20 (s, 1H), 8.49 (s, 1H), 8.66 (s, 1H). |

TABLE 5-continued

| Ex | Structure | IUPAC Name | MS (M + 1) | H¹ NMR 500 MHz, CDCl₃ |
|---|---|---|---|---|
| 57 | 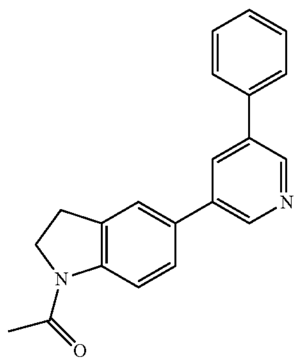 [SMILES: CC(=O)N1CCc2cc(-c3cncc(-c4ccccc4)c3)ccc21] | 1-acetyl-5-(5-phenylpyridin-3-yl)-2,3-dihydro-1H-indole | 315.37 | δ 2.26 (s, 3H), 3.29 (t, J = 8.4 Hz, 2H), 4.13 (t, J = 8.4(Hz, 2H), 7.42-7.52 m, 5H), 7.64 (m, 2H), 8.03 (d, J = 2.0 Hz,1H), 8.32 (d, J = 8.3 Hz,1H), 8.79 (m, 2H). |
| 58 | 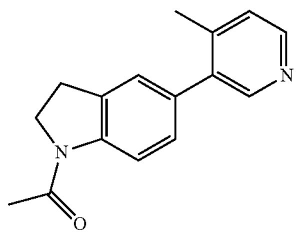 [SMILES: CC(=O)N1CCc2cc(-c3cnccc3C)ccc21] | 1-acetyl-5-(4-methylpyridin-3-yl)-2,3-dihydro-1H-indole | 253.33 | δ 2.25 (s, 3H), 2.29 (s, 3H), 3.26 (t, J = 8.5 Hz, 2H), 4.12 (t, J = 8.5 Hz, 2H), 7.12-7.18 (m, 3H), 8.27 (d, J = 8.2 Hz,1H), 8.41 (m, 2H). |

Assay Description and Results

Methods for V79-Human-CYP11B2 and V79-Human-CYP11B1 Assays:

V79 cell lines stably expressing the either the human CYP11B2 or the human CYP11B1 enzyme were generated using a standard transfection protocol. V79 cells were transfected with plasmids pTriEx3-Hygro-hCyp11B2 or pTriEx3-Hygro-hCyp11B1 using Lipofectamine2000 reagent. V79 cells that stably express the human CYP11B2 or human CYP11B1 enzyme were selected for and maintained in DMEM supplemented with 10% FBS and 400 µg/mL hygromycin for 2 weeks. Single cell clones were generated by infinite dilution in DMEM supplemented with 10% FBS and 400 µg/mL hygromycin until single colonies were obtained. Clones V79-hCYP11B2-CLE9 and V79-hCYP11B1-CL8C7, were determined to produce the most aldosterone and cortisol, respectively, and were selected for inhibitor screening. For testing of inhibitors, cells were harvested at 80% confluency with 0.05% Trypsan-EDTA, washed once in PBS, and reconstituted in DMEM+0.1% BSA media at a cell concentration of 600,000 cells/mL for the CYP11B2 assay and 280,000 cells/mL for the CYP11B1 assay. 25 µL of cells were added to a 384 well tissue culture treated plate and mixed with 0.3 µL of inhibitor or DMSO (1% final DMSO concentration) for 1 hour at 37° C., 5% CO₂. After pre-incubation with inhibitor, the reaction was initiated by adding 5 µL of substrate (final concentration of 125 nM 11-deoxycorticosterone for the CYP11B2 assay or 250 nM 11-deoxycortisol for the CYP11B1 assay). The reaction was carried out for 3 hours at 37° C., 5% CO₂ and was stopped by harvesting the supernatants. The amount of product in the supernatant (aldosterone for CYP11B2 assay and cortisol for the CYP11B1 assay) was measured using HTRF-based assay kit (Aldosterone HTRF-CisBio#64ALDPEB, Cortisol HTRF-CisBio #63IDC002-CORT). $IC_{50}$s for the inhibitor were determined by plotting the amount of product formed against the concentration of inhibitor using sigmoidal dose-response curve (variable slope) fit in GraphPad.

The compounds of Examples 1-20 and 35-49 were tested in the V79-Human-CYP11B2 cell assay and found to have $IC_{50}$s for inhibition of human CYP11B2 of less than 10000 nM. A sub-group of compounds had $IC_{50}$s less than or equal to 250 nM, and a further sub-group of compounds had $IC_{50}$s less than or equal to 50 nM.

The compounds of Examples 1-20 and 35-49 were also tested in the V79-Human-CYP11B1 cell assay. A sub-group of compounds were at least 10-fold more selective for inhibition of CYP11B2 as compared to CYP11B1, and a further sub-group of compounds were at least 30-fold more selective for inhibition of CYP11B2. Representative examples of data collected for compounds of the present invention are shown in Table 6 below.

TABLE 6

| Example | IUPAC Name | V79 Human CYP11B2 $IC_{50}$ (nM) | V79 Human CYP11B1 $IC_{50}$ (nM) |
|---|---|---|---|
| 1 | 1-(5-(5-fluoropyridin-3-yl)indolin-1-yl)ethanone | 110 | >10,000 |
| 43 | 1-(7-chloro-5-(pyridin-3-yl)indolin-1-yl)ethanone | 7.4 | 570 |
| 2 | 1-(7-chloro-5-(5-fluoropyridine-3-yl)indolin-1-yl)ethanone | 12 | 7,900 |
| 3 | 1-(7-chloro-5-(5-methoxypyridin-3-yl)indolin-1-yl)ethanone | 4.1 | 130 |
| 7 | 1-(7-chloro-5-(4-(trifluoromethyl)pyridine-3-yl)indolin-1-yl)ethanone | 5.0 | 610 |
| 10 | 5-(1-acetyl-7-chloroindolin-5-yl)4-methylnicotinotrile | 35 | 1,600 |
| 11 | 1-(7-chloro-5-(isoquinolin-4-yl) indolin-1-yl)ethanone | 0.7 | 60 |
| 6 | 1-(7-chloro-5-(5-(trifluoromethyl)pyridine-3-yl)indolin-1-yl)ethanone | 7.5 | 400 |

TABLE 6-continued

| Example | IUPAC Name | V79 Human CYP11B2 IC$_{50}$ (nM) | V79 Human CYP11B1 IC$_{50}$ (nM) |
|---|---|---|---|
| 4 | (S)-1-(7-chloro-5-(5-(1,1,1,-trifluoro-2-hydroxypropan-2-yl)pyridine-3-yl)indolin-1-yl)ethanone | 1.2 | 26 |
| 5 | (R)-1-(7-chloro-5-(5-(1,1,1,-trifluoro-2hydroxypropan-2-yl)pyridine-3-yl)indolin-1-yl)ethanone | 2.4 | 53 |
| 9 | 1-(7-chloro-5-(4-ethyl-5-fluoropyridin-3-yl)indolin-1-yl)ethanone | 2.3 | 400 |
| 8 | 1-(7-chloro-5-(5-fluoro-4-methylpyridin-3-yl)indolin-1-yl)ethanone | 1.4 | 270 |
| 12 | 1-(7-fluoro-5-(pyridine-3-yl)indolin-1-yl) ethanone | 4.9 | 900 |
| 18 | 1-(7-fluoro-5-(5-fluoropyridine-3-yl)indolin-1-yl)-ethanone | 15 | 1,100 |
| 19 | 1-(7-fluoro-5-(5-fluoro-4-methylpyridin-3-yl)indolin-1-yl)-ethanone | 1.0 | 100 |
| 20 | 1-(5-(4-ethyl-5-fluoropyridine-3-yl)-7-fluoroindolin-1-yl)ethanone | 1.6 | 500 |
| 14 | (R)-1-(7-fluoro-5-(5-(1,1,1-trifluoro-2-hydroxypropan-2-yl)pyridin-3-yl)indolin-1-yl)ethanone | 0.8 | 13 |
| 13 | (S)-1-(7-fluoro-5-(5-(1,1,1-trifluoro-2-hydroxypropan-2-yl)pyridin-3-yl)indolin-1-yl)ethanone | 2.1 | 23 |
| 16 | 5-(1-acetyl-7-fluoroindolin-5-yl)nicotinonitrile | 97 | >10,000 |
| 17 | 5-(1-acetyl-7-fluoroindolin-5-yl)-4-methylnicotinonitrile | 12 | 540 |
| 15 | 1-(7-fluoro-5-(4-methylpyridin-3-yl)indolin-1-yl)ethanone | 0.2 | 68 |
| 47 | 1-(6-fluoro-5-(pyridin-3-yl)indolin-1-yl)ethanone | 180 | 380 |
| 48 | 1-(5-(4-ethyl-5-fluoropyridin-3-yl)-6-fluoroindolin-1-yl)ethanone | 690 | >10,000 |
| 49 | 1-(5-(4-ethyl-5-fluoropyridin-3-yl)-6-fluoroindolin-1-yl)ethanone | 170 | 4,000 |
| 44 | 1-(6-chloro-5-(pyridin-3-yl)indoline-1-yl)ethanone | 640 | 470 |
| 45 | 1-(6-chloro-5-(5-fluoropyridine-3-yl)indolin-1-yl)ethanone | 810 | 760 |
| 46 | 1-(6-chloro-5-(4-ethyl-5-fluoropyridine-3-yl)indolin-1-yl)ethanone | 620 | 780 |

Compounds 21-34 and 50-58 were assayed with a modified protocol from the one described above and found to have IC$_{50}$s for inhibition of human CYP11B2 of less than 10000 nM. For the CYP11B2 assay, cells were reconstituted in DMEM+0.1% BSA media at a cell concentration of 600,000 cells/mL and for the CYP11B1 assay cells were reconstituted in DMEM+0.1% BSA media at a cell concentration of 280,000 cells/mL. 25 µl of cells were added to a 384 well tissue culture treated plate and mixed with 0.30 of inhibitor or DMSO (1% final DMSO concentration) for 1 hour at 37° C., 5% CO$_2$.

Representative examples of data collected for some of compounds of the present invention using this modified procedure are shown in Table 7 below.

TABLE 7

| Example | IUPAC Name | V79 Human CYP11B2 IC$_{50}$ (nM) | V79 Human CYP11B1 IC$_{50}$ (nM) |
|---|---|---|---|
| 21 | 1-propanoyl-5-pyridin-3-yl-2,3-dihydro-1H-indole | 228 | 4737 |
| 22 | 1-(3-chloropropanoyl)-5-pyridin-3-yl-2,3-dihydro-1H-indole | >5000 | >5000 |
| 23 | 1-(cyclopropylcarbonyl)-5-pyridin-3-yl-2,3-dihydro-1H-indole | 1285 | 1423 |
| 24 | 1-[(4-fluorophenyl)carbonyl]-5-pyridin-3-yl-2,3-dihydro-1H-indole | 2833 | >5000 |
| 25 | 1-[(4-methoxyphenyl)carbonyl]-5-pyridin-3-yl-2,3-dihydro-1H-indole | 1433 | >5000 |
| 26 | 1-(phenylacetyl)-5-pyridin-3-yl-2,3-dihydro-1H-indole | 3070 | >5000 |
| 27 | 5-pyridin-3-yl-1-(thiophen-2-ylcarbonyl)-2,3-dihydro-1H-indole | >5000 | 1523 |
| 28 | 4-(1-acetyl-2,3-dihydro-1H-indol-5-yl)isoquinoline | 0.7 | 52 |
| 29 | 4-(1-propanoyl-2,3-dihydro-1H-indol-5-yl)isoquinoline | 2.8 | 516 |
| 30 | 4-[1-(2-methylpropanoyl)-2,3-dihydro-1H-indol-5-yl]isoquinoline | 30 | 3723 |
| 31 | 4-[1-(cyclopropylcarbonyl)-2,3-dihydro-1H-indol-5-yl]isoquinoline | 152 | 6093 |
| 32 | 1-(7-chloro-5-(5-fluoropyridin-3-yl)indolin-1-yl)-2,2,2-trifluoroethanone | 10.6 | 525 |
| 33 | 2,2,2-trifluoro-1-(7-fluoro-5-(5-fluoropyridin-3-yl)indolin-1-yl)ethanone | 17.4 | 1414 |
| 34 | 1-(5-(pyridin-3-yl)indolin-1-yl)ethanethione | 6 | 3383 |
| 50 | 1-acetyl-5-pyridin-3-yl-1H-indole | 23 | 1379 |
| 51 | 4-(1-acetyl-1H-indol-5-yl)isoquinoline | 0.6 | 34 |
| 52 | 1-acetyl-5-(5-fluoropyridin-3-yl)-2,3-dihydro-1H-indole | 61 | 6812 |
| 53 | 5-(1-acetyl-2,3-dihydro-1H-indol-5-yl)pyridine-3-carbonitrile | 426 | 6642 |
| 54 | 1-acetyl-5-(5-methoxypyridin-3-yl)-2,3-dihydro-1H-indole | 16 | 803 |
| 55 | 1-[5-(1-acetyl-2,3-dihydro-1H-indol-5-yl)pyridin-3-yl]ethanone | 36 | 3125 |
| 56 | 1-[5-(1-acetyl-2,3-dihydro-1H-indol-5-yl)pyridin-3-yl]ethanol | 55 | 3756 |
| 57 | 1-acetyl-5-(5-phenylpyridin-3-yl)-2,3-dihydro-1H-indole | 3.0 | 160 |
| 58 | 1-acetyl-5-(4-methylpyridin-3-yl)-2,3-dihydro-1H-indole | 2.2 | 366 |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

We claim:
1. A compound of the formula

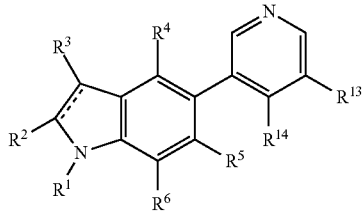

or a pharmaceutically acceptable salt thereof
wherein:
- $R^1$ is —C(O)$R^7$; —C(O)N($R^{11}$)($R^{12}$); —C(S)$R^7$; —S(O)$_2R^7$; cycloalkyl, which is optionally substituted one or more times by halogen, alkyl or haloalkyl; aryl optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; arylalkyl, wherein the aryl ring is optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; heteroaryl optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; or arylalkylcarbonyl, wherein the aryl ring is optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$;
- $R^2$ is H; halogen; —CN; —O$R^7$; —N($R^{10}$)C(O)$R^7$; —N$R^{11}R^{12}$; —C(O)$R^7$; —C(O)N($R^{11}$)($R^{12}$); —N($R^{10}$)C(O)—$R^7$; —C(O)O$R^7$; —OC(O)$R^7$; —SO$_2$N($R^{11}$)($R^{12}$); —N($R^{10}$)SO$_2$—$R^7$; —S(O)$_m$—$R^7$; alkyl optionally substituted one or more times by halogen, —O$R^7$, N$R^8R^9$, —CN, —N($R^{10}$)C(O)$R^7$, —C(O)N($R^8$)($R^9$), —C(O)$R^7$, —C(O)O$R^7$, —OC(O)$R^7$, —SO$_2$N($R^8$)($R^9$), —N($R^{10}$)SO$_2$—$R^7$ or —S(O)$_m$—$R^7$; cycloalkyl optionally substituted one or more times by halogen, alkyl, haloalkyl, —O$R^7$, —N$R^8R^9$, —CN, —N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; heterocycloalkyl optionally substituted one or more times by halogen, alkyl, haloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; aryl optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)$R^7$, —C(O)O$R^7$, —OC(O)$R^7$, —SO$_2$N($R^8$)($R^9$), —N($R^{10}$)SO$_2$—$R^7$ or —S(O)$_m$—$R^7$; or heteroaryl optionally substituted one or more times by halogen, alkyl, haloalkyl, cycloalkyl, —O$R^7$, —CN, —N$R^8R^9$, —N($R^{10}$)C(O)$R^7$, —C(O)N($R^8$)($R^9$), —C(O)$R^7$, —C(O)O$R^7$, —OC(O)$R^7$, —SO$_2$N($R^8$)($R^9$), —N($R^{10}$)SO$_2$—$R^7$ or —S(O)$_m$—$R^7$;
- $R^3$ is H; halogen; —CN; —O$R^7$; —N($R^{10}$)C(O)$R^7$; —N$R^{11}R^{12}$; —C(O)$R^7$; —C(O)N($R^{11}$)($R^{12}$); —N($R^{10}$)C(O)—$R^7$; —C(O)O$R^7$; —OC(O)$R^7$; —SO$_2$N($R^{11}$)($R^{12}$); —N($R^{10}$)SO$_2$—$R^7$; —S(O)$_m$—$R^7$; alkyl optionally substituted one or more times by halogen, —O$R^7$, N$R^8R^9$, —CN, —N($R^{10}$)C(O)$R^7$, —C(O)N($R^8$)($R^9$), —C(O)$R^7$, —C(O)O$R^7$, —OC(O)$R^7$, —SO$_2$N($R^8$)($R^9$), —N($R^{10}$)SO$_2$—$R^7$ or —S(O)$_m$—$R^7$; cycloalkyl optionally substituted one or more times by halogen, alkyl, haloalkyl, —O$R^7$, —N$R^8R^9$, —CN, —N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; heterocycloalkyl optionally substituted one or more times by halogen, alkyl, haloalkyl, —O$R^7$, —CN, —N$R^8R^9$—N($R^{10}$)C(O)$R^7$, —C(O)N($R^8$)($R^9$), —C(O)O$R^7$, —SO$_2$N($R^8$)($R^9$), —N($R^{10}$)SO$_2$—$R^7$ or —S(O)$_m$—$R^7$; aryl optionally substituted one or more times by halogen, alkyl, haloalkyl, cycloalkyl, —O$R^7$, —CN, —N$R^8R^9$—N($R^{10}$)C(O)$R^7$, —C(O)N($R^8$)($R^9$), —C(O)$R^7$, —C(O)O$R^7$, —OC(O)$R^7$, —SO$_2$N($R^8$)($R^9$), —N($R^{10}$)SO$_2$—$R^7$ or —S(O)$_m$—$R^7$; or heteroaryl optionally substituted one or more times by halogen, alkyl, haloalkyl, cycloalkyl, —O$R^7$, —CN, —N$R^8R^9$, —N($R^{10}$)C(O)$R^7$, —C(O)N($R^8$)($R^9$), —C(O)$R^7$, —C(O)O$R^7$, —OC(O)$R^7$, —SO$_2$N($R^8$)($R^9$), —N($R^{10}$)SO$_2$—$R^7$ or —S(O)$_m$—$R^7$;
- $R^4$ is H; halogen; —CN; alkyl optionally substituted one or more times by halogen or cycloalkyl optionally substituted once or twice by alkyl or halogen; or cycloalkyl optionally substituted once or twice by alkyl or halogen;
- $R^5$ is H; halogen; —CN; alkyl optionally substituted one or more times by halogen or cycloalkyl optionally substituted once or twice by alkyl or halogen; or cycloalkyl optionally substituted once or twice by alkyl or halogen;
- $R^6$ is H; halogen; —CN; alkyl optionally substituted one or more times by halogen or cycloalkyl optionally substituted once or twice by alkyl or halogen; or cycloalkyl optionally substituted once or twice by alkyl or halogen;
- $R^7$ is independently H; alkyl optionally substituted one or more times by halogen, —O$R^{10}$, —N$R^8R^9$, —CN, —N($R^{10}$)C(O)$R^{10}$, —C(O)N($R^8$)($R^9$), —C(O)$R^{10}$, —C(O)O$R^{10}$ or —S(O)$_m$—$R^{10}$; cycloalkyl optionally substituted one or more times by halogen, alkyl, haloalkyl, —O$R^{10}$, —N$R^8R^9$, —CN, —N($R^{10}$)C(O)$R^{10}$, —C(O)N($R^8$)($R^9$), —C(O)O$R^{10}$ or —S(O)$_m$—$R^{10}$; aryl optionally substituted one or more times by halogen, alkyl, haloalkyl, cycloalkyl, —O$R^{10}$, —N$R^8R^9$, —CN, —N($R^{10}$)C(O)$R^{10}$, —C(O)N($R^8$)($R^9$), —C(O)$R^{10}$, —C(O)O$R^{10}$—OC(O)$R^{10}$, or —S(O)$_m$—$R^{10}$; or heteroaryl optionally substituted one or more times by halogen, alkyl, haloalkyl, cycloalkyl, —O$R^{10}$, —N$R^8R^9$, —CN, —N($R^9$)C(O)$R^{10}$, —C(O)N($R^8$)($R^9$), —C(O)$R^{10}$, —C(O)O$R^{10}$—OC(O)$R^{10}$ or —S(O)$_m$—$R^{10}$;
- $R^8$ is independently H or alkyl;
- $R^9$ is independently H or alkyl;
- or $R^8$ and $R^9$ are joined together with the nitrogen to which they are attached form a saturated 5- to 7-membered heterocyclic ring;
- $R^{10}$ is independently H, alkyl or haloalkyl;
- $R^{11}$ is independently H; alkyl optionally substituted one or more times by halogen, —O$R^7$, —N$R^8R^9$, —CN, —N($R^{10}$)C(O)$R^7$, —C(O)N($R^8$)($R^9$), —C(O)$R^7$, —C(O)O$R^7$ or —S(O)$_m$—$R^7$; cycloalkyl optionally substituted one or more times by halogen, alkyl, haloalkyl, —O$R^7$, —N$R^8R^9$, —CN, —N($R^{10}$)C(O)$R^7$, —C(O)N($R^8$)($R^9$), —C(O)O$R^8$ or —S(O)$_m$—$R^8$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)R$^7$, —C(O)OR$^7$, —OC(O)R$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$;

R$^{12}$ is independently H; alkyl optionally substituted one or more times by halogen, —OR$^7$, —NR$^8$R$^9$, —CN, —N(R$^{10}$)C(O)R$^7$, —C(O)N(R$^8$)(R$^9$), —C(O)R$^7$, —C(O)OR$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^8$ or —S(O)$_m$—R$^8$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)R$^7$, —C(O)OR$^7$, —OC(O)R$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$ or —S(O)$_m$—R$^7$; or R$^{11}$ and R$^{12}$ are joined together with the nitrogen to which they are attached form a saturated 5- to 7-membered heterocyclic ring;

R$^{13}$ and R$^{14}$ form a 5-7 membered carbocyclic or heterocyclic ring that is fused to the pyridyl ring to which R$^{13}$ and R$^{14}$ are attached, wherein the ring formed by R$^{13}$ and R$^{14}$ is optionally substituted by 1 to 3 R$^{15}$;

R$^{15}$ is independently H; halogen; —CN; —OR$^7$; —C(O)N(R$^8$)(R$^9$); —C(O)R$^7$; —C(O)OR$^7$; —OC(O)R$^7$; —SO$_2$N(R$^8$)(R$^9$); —N(R$^{10}$)SO$_2$—R$^7$; —S(O)$_m$—R$^7$; alkyl optionally substituted one or more times by halogen, —OR$^7$, —NR$^8$R$^9$, —CN, —N(R$^{11}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)S(O)$_2$—R$^7$, or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^8$, —SO$_2$N(R$^8$)(R$^9$), —N(R$^{10}$)SO$_2$—R$^7$ or —S(O)$_m$—R$^7$; aryl optionally substituted one or more times by halogen, alkyl, haloalkyl, cycloalkyl, —OR$^7$, —CN, —NR$^8$R$^9$, —N(R$^{10}$)C(O)(R$^7$), —C(O)N(R$^8$)(R$^9$), —C(O)R$^7$—C(O)OR$^7$, —OC(O)R$^7$, —SO$_2$N(R$^8$)(R$^9$), —N(R$^{10}$)SO$_2$—R$^7$, or —S(O)$_m$—R$^7$; heterocycloalkyl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)R$^7$, —C(O)OR$^7$, —OC(O)R$^7$, —SO$_2$N(R$^8$)(R$^9$), —N(R$^{10}$)SO$_2$—R$^7$ or —S(O)$_m$—R$^7$;

══ is a single or double bond; and
m is 0, 1 or 2.

2. The compound as defined in claim 1 or a pharmaceutically acceptable salt thereof, wherein:
R$^1$ is —C(O)R$^7$, —C(O)N(R$^{11}$)(R$^{12}$), —C(S)—R$^7$ or benzoyl, which is optionally substituted once or twice by alkyl, halogen, alkoxy or haloalkyl;
R$^2$ is H;
R$^3$ is H;
R$^4$ is H;
R$^5$ is H or halogen;
R$^6$ is H or halogen;
R$^7$ is H, alkyl, haloalkyl, cycloalkyl or phenyl optionally substituted once or twice by halogen, —OH, alkoxy or haloalkoxy, or heteroaryl;
R$^{11}$ is H;
R$^{12}$ is alkyl, phenyl or phenyl substituted once or twice by halogen, OH, alkoxy or haloalkoxy;
R$^{13}$ and R$^{14}$ are joined together with the pyridine ring to which they are attached form

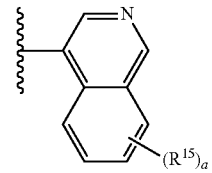

where:
R$^{15}$ is alkyl or halogen; and
a is 0, 1 or 2.

3. The compound as defined in claim 1 or a pharmaceutically acceptable salt thereof, which has the structural formula

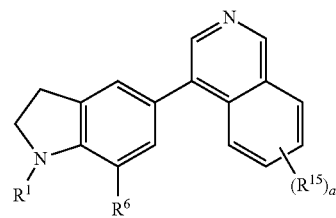

V wherein:
R$^1$ is —C(O)R$^7$;
R$^6$ is H or halogen;
R$^7$ is alkyl, haloalkyl, phenyl or phenyl substituted one or twice by halogen, —OH, alkoxy or haloalkoxy;
R$^{15}$ is alkyl or halogen; and
a is 0, 1 or 2.

4. The compound as defined in claim 1 or a pharmaceutically acceptable salt thereof, which has the structural formula

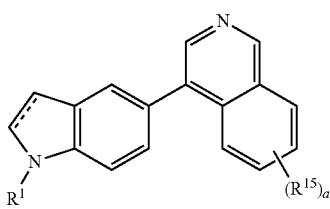

VII wherein R$^1$ is —C(O)R$^7$, —C(S)R$^7$ or benzoyl, which is optionally substituted once or twice by alkyl, halogen, alkoxy or haloalkyl;

R⁷ is alkyl, haloalkyl, cycloalkyl, phenyl, phenyl substituted once or twice by halogen or alkoxy;
R¹⁵ is alkyl or halo; and
a is 0, 1 or 2.

5. A compound, or a pharmaceutically acceptable salt thereof, selected from the group consisting of:
4-(1-acetyl-2,3-dihydro-1H-indol-5-yl)isoquinoline;
4-(1-propanoyl-2,3-dihydro-1H-indol-5-yl)isoquinoline;
4-[1-(2-methylpropanoyl)-2,3-dihydro-1H-indol-5-yl]isoquinoline;
4-[1-(cyclopropylcarbonyl)-2,3-dihydro-1H-indol-5-yl]isoquinoline; and
4-(1-acetyl-1H-indol-5-yl)isoquinoline.

6. A pharmaceutical composition comprising a therapeutically effective amount of at least one compound of Formula I as defined in claim 1 or a pharmaceutically acceptable salt thereof and a pharmaceutically acceptable carrier.

7. A pharmaceutical composition comprising a therapeutically effective amount of at least one compound of Formula I as defined in claim 1 or a pharmaceutically acceptable salt thereof, a therapeutically effective amount of at least one additional therapeutic agent and a pharmaceutically acceptable carrier.

8. A method for the treatment or amelioration of one or more conditions associated with inhibiting CYP11B2 comprising hypertension, heart failure, hypokalemia, and post-myocardial infarction, which comprises administering a therapeutically effective amount at least one compound of Formula I as defined in claim 1 or a pharmaceutically acceptable salt thereof to a mammal in need of such treatment.

9. A method for inhibiting CYP11B2 in a mammal in need thereof, which comprises administering an effective amount of a compound of the formula

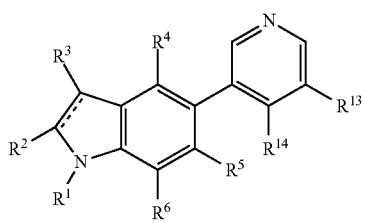

or a pharmaceutically acceptable salt thereof
wherein:
R¹ is —C(O)R⁷; —C(O)N(R¹¹)(R¹²); —C(S)R⁷; —S(O)₂R⁷; cycloalkyl, which is optionally substituted one or more times by halogen, alkyl or haloalkyl; aryl optionally substituted one or more times by halogen, alkyl, haloalkyl, cycloalkyl, —OR⁷, —CN, —NR⁸R⁹—N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; arylalkyl, wherein the aryl ring is optionally substituted one or more times by halogen, alkyl, haloalkyl, cycloalkyl, —OR⁷, —CN, —NR⁸R⁹—N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; heteroaryl optionally substituted one or more times by halogen, alkyl, haloalkyl, cycloalkyl, —OR⁷, —CN, —NR⁸R⁹—N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; arylalkylcarbonyl, wherein the aryl ring is optionally substituted one or more times by halogen, alkyl, haloalkyl, —OR⁷, —CN, —NR⁸R⁹—N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷;

R² is H; halogen; —CN; —OR⁷; —N(R¹⁰)C(O)R⁷; —NR¹¹R¹²; —C(O)R⁷; —C(O)N(R¹¹)(R¹²); —N(R¹⁰)C(O)—R⁷; —C(O)OR⁷; —OC(O)R⁷; —SO₂N(R¹¹)(R¹²); —N(R¹⁰)SO₂—R⁷; —S(O)ₘ—R⁷; alkyl optionally substituted one or more times by halogen, —OR⁷, NR⁸R⁹, —CN, —N(R¹⁰)C(O)R⁷, —C(O)N(R⁸)(R⁹), —C(O)R⁷, —C(O)OR⁷, —OC(O)R⁷, —SO₂N(R⁸)(R⁹), —N(Ro)SO₂—R⁷ or —S(O)ₘ—R; cycloalkyl optionally substituted one or more times by halogen, alkyl, haloalkyl, —OR⁷, —NR⁸R⁹, —CN, —N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; heterocloalkyl optionally substituted one or more times by halogen, alkyl, haloalkyl, —OR⁷, —CN, —NR⁸R⁹—N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; aryl optionally substituted one or more times by halogen, alkyl, haloalkyl, cycloalkyl, —OR⁷, —CN, —NR⁸R⁹—N(R¹⁰)C(O)R⁷, —C(O)N(R⁸)(R⁹), —C(O)R⁷, —C(O)OR⁷, —OC(O)R⁷, —SO₂N(R⁸)(R⁹), —N(R¹⁰)SO₂—R⁷ or —S(O)ₘ—R⁷; or heteroaryl optionally substituted one or more times by halogen, alkyl, haloalkyl, cycloalkyl, —OR⁷, —CN, —NR⁸R⁹, —N(R¹⁰)C(O)R⁷, —C(O)N(R⁸)(R⁹), —C(O)R⁷, —C(O)OR⁷, —OC(O)R⁷, —SO₂N(R⁸)(R⁹), —N(R¹⁰)SO₂—R⁷ or —S(O)ₘ—R⁷;

R³ is H; halogen; —CN; —OR⁷; —N(R¹⁰)C(O)R⁷; —NR¹¹R¹²; —C(O)R⁷; —C(O)N(R¹¹)(R¹²); —N(R¹⁰)C(O)—R⁷; —C(O)OR⁷; —OC(O)R⁷; —SO₂N(R¹¹)(R¹²); —N(R¹⁰)SO₂—R⁷; —S(O)ₘ—R⁷; alkyl optionally substituted one or more times by halogen, —OR⁷, NR⁸R⁹, —CN, —N(R¹⁰)C(O)R⁷, —C(O)N(R⁸)(R⁹), —C(O)R⁷, —C(O)OR⁷, —OC(O)R⁷, —SO₂N(R⁸)(R⁹), —N(R¹⁰)SO₂—R⁷ or —S(O)ₘ—R⁷; cycloalkyl optionally substituted one or more times by halogen, alkyl, haloalkyl, —OR⁷, —NR⁸R⁹, —CN, —N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; heterocloalkyl optionally substituted one or more times by halogen, alkyl, haloalkyl, —OR⁷, —CN, —NR⁸R⁹—N(R¹⁰)C(O)R⁷, —C(O)N(R⁸)(R⁹), —C(O)OR⁷, —SO₂N(R⁸)(R⁹), —N(R¹⁰)SO₂—R⁷ or —S(O)ₘ—R⁷; aryl optionally substituted one or more times by halogen, alkyl, haloalkyl, cycloalkyl, —OR⁷, —CN, —NR⁸R⁹—N(R¹⁰)C(O)R⁷, —C(O)N(R⁸)(R⁹), —C(O)R⁷, —C(O)OR⁷, —OC(O)R⁷, —SO₂N(R⁸)(R⁹), —N(R¹⁰)SO₂—R⁷ or —S(O)ₘ—R⁷; or heteroaryl optionally substituted one or more times by halogen, alkyl, haloalkyl, cycloalkyl, —OR⁷, —CN, —NR⁸R⁹, —N(R¹⁰)C(O)R⁷, —C(O)N(R⁸)(R⁹), —C(O)R⁷, —C(O)OR⁷, —OC(O)R⁷, —SO₂N(R⁸)(R⁹), —N(R¹⁰)SO₂—R⁷ or —S(O)ₘ—R⁷;

R⁴ is H; halogen; —CN; alkyl optionally substituted one or more times by halogen or cycloalkyl optionally substituted once or twice by alkyl or halogen; or cycloalkyl optionally substituted once or twice by alkyl or halogen;

R⁵ is H; halogen; —CN; alkyl optionally substituted one or more times by halogen or cycloalkyl optionally substituted once or twice by alkyl or halogen; or cycloalkyl optionally substituted once or twice by alkyl or halogen;

R⁶ is H; halogen; —CN; alkyl optionally substituted one or more times by halogen or cycloalkyl optionally substituted once or twice by alkyl or halogen; or cycloalkyl optionally substituted once or twice by alkyl or halogen;

$R^7$ is independently H; alkyl optionally substituted one or more times by halogen, —$OR^{10}$, —$NR^8R^9$, —CN, —$N(R^{10})C(O)R^{10}$, —$C(O)N(R^8)(R^9)$, —$C(O)R^{10}$, —$C(O)OR^{10}$ or —$S(O)_m$—$R^{10}$ cycloalkyl optionally substituted one or more times by halogen, alkyl, haloalkyl, —$OR^{10}$, —$NR^8R^9$, —CN, —$N(R^{10})C(O)R^{10}$, —$C(O)N(R^8)(R^9)$, —$C(O)OR^{10}$ or —$S(O)_m$—$R^{10}$; aryl optionally substituted one or more times by halogen, alkyl, haloalkyl, cycloalkyl, —$OR^{10}$, —$NR^8R^9$, —CN, —$N(R^{10})C(O)R^{10}$, —$C(O)N(R^8)(R^9)$, —$C(O)R^{10}$, —$C(O)OR^{10}$—$OC(O)R^{10}$, or —$S(O)_m$—$R^{10}$; or heteroaryl optionally substituted one or more times by halogen, alkyl, haloalkyl, cycloalkyl, —$OR^{10}$, —$NR^8R^9$, —CN, —$N(R^9)C(O)R^{10}$, —$C(O)N(R^8)(R^9)$, —$C(O)R^{10}$, —$C(O)OR^{10}$—$OC(O)R^{10}$ or —$S(O)_m$—$R^{10}$;

$R^8$ is independently H or alkyl;

$R^9$ is independently H or alkyl;

or $R^8$ and $R^9$ are joined together with the nitrogen to which they are attached form a saturated 5- to 7-membered heterocyclic ring;

$R^{10}$ is independently H, alkyl or haloalkyl;

$R^{11}$ is independently H; alkyl optionally substituted one or more times by halogen, —$OR^7$, —$NR^8R^9$, —CN, —$N(R^{10})C(O)R^7$, —$C(O)N(R^8)(R^9)$, —$C(O)R^7$, —$C(O)OR^7$ or —$S(O)_m$—$R^7$; cycloalkyl optionally substituted one or more times by halogen, alkyl, haloalkyl, —$OR^7$, —$NR^8R^9$, —CN, —$N(R^{10})C(O)R^7$, —$C(O)N(R^8)(R^9)$, —$C(O)OR^8$ or —$S(O)_m$—$R^8$; aryl optionally substituted one or more times by halogen, alkyl, haloalkyl, cycloalkyl, —$OR^7$, —CN, —$NR^8R^9$—$N(R^{10})C(O)(R^7)$, —$C(O)N(R^7)(R^8)$, —$C(O)R^7$, —$C(O)OR^7$, —$OC(O)R^7$ or —$S(O)_m$—$R^7$; heterocycloalkyl optionally substituted one or more times by halogen, alkyl, haloalkyl, —$OR^7$, —CN, —$NR^8R^9$—$N(R^{10})C(O)R^7$, —$C(O)N(R^8)(R^9)$, —$C(O)R^7$, —$C(O)OR^7$, —$OC(O)R^7$ or —$S(O)_m$—$R^7$; or heteroaryl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)R^7$, —$C(O)OR^7$, —$OC(O)R^7$ or —$S(O)_m$—$R^7$;

$R^{12}$ is independently H; alkyl optionally substituted one or more times by halogen, —$OR^7$, —$NR^8R^9$, —CN, —$N(R^{10})C(O)R^7$, —$C(O)N(R^8)(R^9)$, —$C(O)R^7$, —$C(O)OR^7$ or —$S(O)_m$—$R^7$; cycloalkyl optionally substituted one or more times by halogen, alkyl, haloalkyl, —$OR^7$, —$NR^8R^9$, —CN, —$N(R^{10})C(O)R^7$, —$C(O)N(R^8)(R^9)$, —$C(O)OR^8$ or —$S(O)_m$—$R^8$; aryl optionally substituted one or more times by halogen, alkyl, haloalkyl, cycloalkyl, —$OR^7$, —CN, —$NR^8R^9$—$N(R^{10})C(O)(R^7)$, —$C(O)N(R^7)(R^8)$, —$C(O)R^7$, —$C(O)OR^7$, —$OC(O)R^7$ or —$S(O)_m$—$R^7$; heterocycloalkyl optionally substituted one or more times by halogen, alkyl, haloalkyl, —$OR^7$, —CN, —$NR^8R^9$—$N(R^{10})C(O)R^7$, —$C(O)N(R^8)(R^9)$, —$C(O)R^7$, —$C(O)OR^7$, —$OC(O)R^7$ or —$S(O)_m$—$R^7$; or heteroaryl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)R^7$, —$C(O)OR^7$, —$OC(O)R^7$ or —$S(O)_m$—$R^7$;

or $R^{11}$ and $R^{12}$ are joined together with the nitrogen to which they are attached form a saturated 5- to 7-membered heterocyclic ring;

$R^{13}$ and $R^{14}$ form a 5-7 membered carbocyclic or heterocyclic ring that is fused to the pyridyl ring to which $R^{13}$ and $R^{14}$ are attached, wherein the ring formed by $R^{13}$ and $R^{14}$ is optionally substituted by 1 to 3 $R^{15}$;

$R^{15}$ is independently H; halogen; —CN; —$OR^7$; —$C(O)N(R^8)(R^9)$; —$C(O)R^7$; —$C(O)OR^7$; —$OC(O)R^7$; —$SO_2N(R^8)(R^9)$; —$N(R^{10})SO_2$—$R^7$; —$S(O)_m$—$R^7$; alkyl optionally substituted one or more times by halogen, —$OR^7$, —$NR^8R^9$, —CN, —$N(R^{11})C(O)R^7$, —$C(O)N(R^8)(R^9)$, —$C(O)R^7$, —$C(O)OR^7$, —$OC(O)R^7$, —$SO_2N(R^8)(R^9)$, —$N(R^{10})S(O)_2$—$R^7$, or —$S(O)_m$—$R^7$; cycloalkyl optionally substituted one or more times by halogen, alkyl, haloalkyl, —$OR^7$, —$NR^8R^9$, —CN, —$N(R^{10})C(O)R^7$, —$C(O)N(R^8)(R^9)$, —$C(O)OR^8$, —$SO_2N(R^8)(R^9)$, —$N(R^{10})SO_2$—$R^7$ or —$S(O)_m$—$R^7$; aryl optionally substituted one or more times by halogen, alkyl, haloalkyl, cycloalkyl, —$OR^7$, —CN, —$NR^8R^9$, —$N(R^{10})C(O)(R^7)$, —$C(O)N(R^8)(R^9)$, —$C(O)R^7$—$C(O)OR^7$, —$OC(O)R^7$, —$SO_2N(R^8)(R^9)$, —$N(R^{10})SO_2$—$R^7$, or —$S(O)_m$—$R^7$; heterocycloalkyl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)R^7$, —$C(O)OR^7$, —$OC(O)R^7$, —$SO_2N(R^8)(R^9)$, —$N(R^{10})SO_2$—$R^7$ or —$S(O)_m$—$R^7$; or heteroaryl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)R^7$, —$C(O)OR^7$, —$OC(O)R^7$, —$SO_2N(R^8)(R^9)$, —$N(R^{10})SO_2$—$R^7$ or —$S(O)_m$—$R^7$;

=== is a single or double bond; and m is 0, 1 or 2.

10. The method according to claim 8 wherein the condition of heart failure is congestive heart failure, diastolic dysfunction, left ventricular diastolic dysfunction, and systolic dysfunction.

* * * * *